US008993607B2

(12) United States Patent
LaVoie et al.

(10) Patent No.: US 8,993,607 B2
(45) Date of Patent: Mar. 31, 2015

(54) THERAPEUTIC COMPOUNDS

(75) Inventors: Edmond J. LaVoie, New Brunswick, NJ (US); Joseph E. Rice, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1427 days.

(21) Appl. No.: 12/671,888

(22) PCT Filed: Aug. 1, 2008

(86) PCT No.: PCT/US2008/072025
§ 371 (c)(1),
(2), (4) Date: Oct. 11, 2011

(87) PCT Pub. No.: WO2009/018551
PCT Pub. Date: Feb. 5, 2009

(65) Prior Publication Data
US 2012/0046234 A1 Feb. 23, 2012

Related U.S. Application Data

(60) Provisional application No. 60/953,648, filed on Aug. 2, 2007.

(51) Int. Cl.
*A61K 31/422* (2006.01)
*A61K 31/4178* (2006.01)
*C07D 263/32* (2006.01)
*C07D 233/64* (2006.01)
*C07D 498/22* (2006.01)

(52) U.S. Cl.
CPC .................................. *C07D 498/22* (2013.01)
USPC ........... 514/375; 540/460; 540/461; 514/183; 514/393; 548/217; 548/301.7

(58) Field of Classification Search
USPC .................. 540/460, 461; 514/183, 375, 393; 548/217, 301.7
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,851,524 A | 7/1989 | Brois et al. | |
| 4,938,949 A | 7/1990 | Borch et al. | |
| 4,992,478 A | 2/1991 | Geria | |
| 8,093,235 B2 | 1/2012 | Lavoie et al. | |
| 2009/0156627 A1 | 6/2009 | Lavoie et al. | |
| 2011/0230531 A1 | 9/2011 | Lavoie et al. | |
| 2012/0071527 A1 | 3/2012 | LaVoie et al. | |
| 2012/0238595 A1 | 9/2012 | LaVoie et al. | |

FOREIGN PATENT DOCUMENTS

| | | |
|---|---|---|
| CA | 2436942 A1 | 6/2002 |
| EP | 1350794 A1 | 10/2003 |
| EP | 1602659 A1 | 12/2005 |
| EP | 2186810 A1 | 5/2010 |
| JP | 11-180997 A | 7/1999 |
| JP | 2006-316008 A | 11/2006 |
| WO | WO 97/48708 A1 | 12/1997 |
| WO | WO 02/48153 A1 | 6/2002 |
| WO | WO 2005/000880 A2 | 1/2005 |
| WO | WO 2007/127173 A2 | 11/2007 |
| WO | WO 2007/127173 A4 | 11/2007 |
| WO | WO 2009/018549 A1 | 2/2009 |
| WO | WO 2009/018551 A2 | 2/2009 |

OTHER PUBLICATIONS

Minhas et al, Bioorganic & Medicinal Chemistry Letters (2006), vol. 16, pp. 3891-3895.*
Sohda et al, Journal of Antibiotics, 2005, vol. 58 (1); pp. 27-31.*
Barbieri, C.M., et al., "Defining the mode, energetic and specificity with which a macrocyclic hexaoxazole binds to human telomeric G-quadruplex DNA", *Nucleic Acids Res.*, 35(10), 3272-3286 (2007).
Bertram et al., "Concise synthesis of stereodefined, thiazole—containing cyclic hexa- and octapeptide relatives of the Lissoclinums, via cyclooligomerisation reactions", *Tetrahedron* vol. 59, No. 35, 6979-6990 (2003).
Binz, N., et al., "Telomerase inhibition, telomere shortening, cell growth suppression and induction of apoptosis by telomestatin in childhood neuroblastoma cells", *Eur. J.Cancer*, 41(18), 2873-2881 (2005).
Chattopadhyay, S.K. and S. Biswas, "Convergent synthesis of a 24-membered macrocyclic hexaoxazole derivative related to the novel telomerase inhibitor telomestatin", *Tetrahedron Letters*, 47(45), 7897-7900 (2006).
Chattopadhyay, "Efficient Construction of Doubly Functionalized Trisoxazole Derivative Relevant to the Synthesis of the Novel Telomerase Inhibitor Telomestatin and its Analogues", *Synthesis*, 1289-1294 (2006).
Database Accession No. 2006:1228832, Database Caplus [Online] Chemical Abstracts Service, Columbus, Ohio, US; XP002659478, 9 pages (2006).
Deeley, "Synthesis and establishment of stereochemistry of the unusual polyoxazole-thiazole based cyclopeptide YM-216391 isolated from Streptomyces nobilis", *Chem. Communications*, 797-799 (2005).
Doi, "Total Synthesis of (R)-Telomestatin", *Organic Letters*, 8, 4165-4167 (2006).
Endoh, "Useful Synthesis of Longer Array Oxazole Rings for Telomestatin", *Heterocycles*, 60, 1567-2572 (2003).
European Patent Office, Supplementary European Search Report and European Opinion, Application No. 08826736.4, 4 pages, Jul. 14, 2010.

(Continued)

*Primary Examiner* — Kamal Saeed
*Assistant Examiner* — Janet L Coppins
(74) *Attorney, Agent, or Firm* — Viksnins Harris & Padys PLLP

(57) ABSTRACT

The invention provides compounds of formula I, II, and III as defined herein, as well as salts thereof. The compounds may have activity as anti-proliferative agents.

35 Claims, No Drawings

(56) References Cited

OTHER PUBLICATIONS

Han et al., "G-quadruplex DNA: a potential target for anti-cancer drug design", *TiPS*, vol. 21, 136-142 (2000).

Jantos, "Oxazole-Based Peptide Macrocycles: A New Class of G-Quadruplex Binding Ligands", *J. Am. Chem. Soc.*, 128, 13662-13663, (2006).

Kim, et al. "Telomestatin, a potent telomerase inhibitor that interacts quite specifically with the human telomeric intramolecular g-quadruplex", *J. Am. Chem. Soc.*, 124, 2098-2099 (2002).

Kim, M., et al., "The Different Biological Effects of Telomestatin and TMPyP4 Can Be Attributed to Their Selectivity for Interaction with Intramolecular or Intermolecular G-Quadruplex Structures", *Cancer Res.*, 63, 3247-3256, (2003).

Liu, W., et al., "Binding of G-Quadruplex—interactive Agents to Distinct G-Quadruplexes Induces Different Biological Effects in MiaPaCa Cells", *Nucleosides, Nucleotides, and Nucleic Acids*, 24, 1801-1815, (2005).

Lucke et al., "Designing supramolecular structures from models of cyclic peptide scaffolds with heterocyclic constraints", *Journal of Molecular Graphics and Modeling*, vol. 21, pp. 341-355 (2003).

Marson, C.M. and M. Saadi, "Synthesis of the penta-oxazole core of telomestatin in a convergent approach to poly-oxazolemacrocycles", *Organic & Biomolecular Chemistry*, 4(21), 3892-3893 (2006).

Minhas, G.S. et al., "Synthesis and G-quadruplex stabilizing properties of a series of oxazole-containing macrocycles", *Bioorganic & Medicinal Chemistry Letters*, 16(15), 3891-3895 (2006).

Nakajima, "Telomerase inhibition enhances apoptosis in human acute leukemia cells: possibility of antitelomerase therapy", *Leukemia*, 17, 560-567 (2003).

Patent Cooperation Treaty, International Search Report and Written Opinion, PCT/US08/072025, 14 pages, Jan. 19, 2009.

Rzuczek et al., "Macrocyclic Pyridyl Polyoxazoles: Selective RNA and DNA G-Quadruplex Ligands as Antitumor Agents", *J. Med. Chem.*, 53, 3632-3644 (2010).

Satyanarayana, M., et al., "Ring-closing metathesis for the synthesis of a highly G-quadruplex selective macrocyclic hexaoxazole having enhanced cytotoxic potency", *Bioorg. Med. Chem. Lett.*, 18(13), 3802-3804 (2008).

Satyanarayana, et al., "Macrocyclic hexaoxazoles: Influence of aminoalkyl substituents on RNA and DNA G-quadruplex stabilization and cytotoxicity", *Bioorg Med. Chem. Lett.*, vol. 20, 3150-3154 (2010).

Shin-Ya, K., et al., "Telomestatin, a Novel Telomerase Inhibitor from *Streptomyces anulatus*", *J. Am. Chem. Soc.*, 123(6), 1262-1263, (2001).

Singh et al., "Novel cylindrical, conical, and macrocyclic peptides from the cyclooligomerization of functionalized thiazole amino acids", *J. Am. Chem. Soc.*, vol. 123, 333-334, including 13 supplemental pages (2001).

Sohda, K, et al., "YM-216391, a Novel Cytotoxic Cyclic Peptide from *Streptomyces nobilis*. I. Fermentation, Isolation and Biological Activities", *J. Antibiotics*, 58(1), 27-31, (2005).

Sohda, K., et al., "YM-216391, a novel cytotoxic cyclic peptide from *Streptomyces nobilis*. II. Physico-chemical properties and structure elucidation", *J. Antibiot.* (Tokyo), 58(1), 32-36, (2005).

Tauchi, T., et al., "Activity of a novel G-quadruplex-interactive telomerase inhibitor, telomestatin (SOT-095), against human leukemia cells: involvement of ATM-dependent DNA damage response pathways", *Oncogene*, 22, 5338-5347, (2003).

Tauchi et al., "Telomerase inhibition with a novel G-quadruplex-interactive agent, telomestatin: in vitro and in vivo studies in acute leukemia", *Oncogene*, 25, 5719-5725 (2006).

Wang, "First Total Synthesis of Leucamide A", *J. Org. Chem.*, 68, 1636-1639, (2003).

\* cited by examiner

THERAPEUTIC COMPOUNDS

PRIORITY OF INVENTION

This application claims priority from U.S. Provisional Application No. 60/953,648, filed 2 Aug. 2007, which application is incorporated by reference.

BACKGROUND OF THE INVENTION

A diverse array of compounds, including anthraquinones, acridines, cationic porphyrins, perylenes, thidium derivatives, fluorenones, pentacyclic acridinium salts, fluoroquinophenoxazines, and other specific miscellaneous polycyclic compounds, have been reported to stabilize G-quadruplex DNA. Most of these compounds have little or no selectivity for G-quadruplex vs. duplex DNA.

Telomestatin is a natural product isolated from *Streptomyces anulatus* 3533-SV4 (Shin-ya et al., *J. Am. Chem. Soc.*, 2001, 123, 1262-1263). At the time of its discovery, telomestatin was viewed as the most potent inhibitor of telomerase. In vitro, telomestatin stabilizes G-quadruplex vs. duplex DNA in a 70:1 ratio (Kim et al., *Cancer Res.*, 2003, 63, 3247-3256). It has been suggested that telomestatin also inhibits telomerase function in vivo, since cells treated with the natural product exhibit a cellular senescence phenotype. Like telomere dysfunction, telomestatin activates the ATM signaling pathway. While the precise mechanism by which telomestatin interacts with a G-quadruplex has not been definitively elucidated, telomestatin does suppress the plating efficiency of K62 leukemia cells but has a much lesser effect on burst-forming units—erythrocyte (BFU-E) and colony-forming units—granulocyte/macrophage (CFU-GM) from natural bone marrow CD34-positive cells (Tauchi et al., *Oncogene*, 2003, 22, 5338-5347).

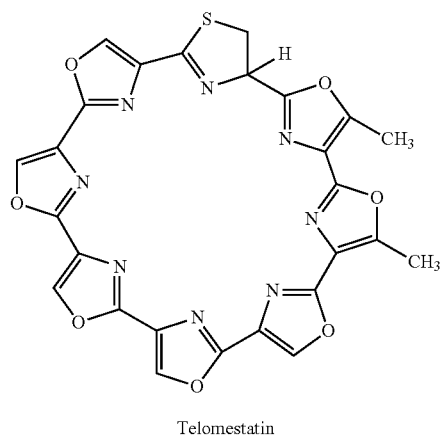 [SMILES: Cc1oc2nc1-c1nc(co1)-c1nc(co1)-c1nc(co1)-c1nc(co1)-c1nc(co1)C1=NC(CS1)c1nc-2c(C)o1]

Telomestatin

The anticancer potential of telomestatin resides in its telomerase inhibitory activity ($IC_{50}$ 5 nM) and in its ability to enhance apoptosis. Telomestatin has been evaluated for cytotoxicity in the human neuroblastoma cell lines SK-N-AS, LANS, WAC2, and LAN1 with $IC_{50}$ values of 0.8, 2.5, 3.2, and 4.0 μM respectively (Binz et al., *Eur. J. Cancer*, 2005, 41, 2873-2881) and in the human pancreatic carcinoma MiaPaCa with an $IC_{50}$ value of 0.5 μM (Liu et al., *Nucleosides, Nucleotides, and Nucleic Acids*, 2005, 24, 1801-1815).

Another macrocyclic polyoxazole, YM-216391 isolated from *Streptomyces nobilis* is active against the human breast cancer cell lines HBC-4, BSY-1, HBC-5, MCF-7, and MDA-MB-231 with $GI_{50}$ values ranging from 15-33 nM (Sohda, K.-y., et al., *J. Antibiotics*, 2005, 58, 27-31 and Sohda, K.-y., et al., Hiramoto, M., Suzumura, K.-i., Takebayashi, Y., Suzuki, K.-i., Tanaka, A. *J. Antibiotics*, 2005, 58, 32-36).

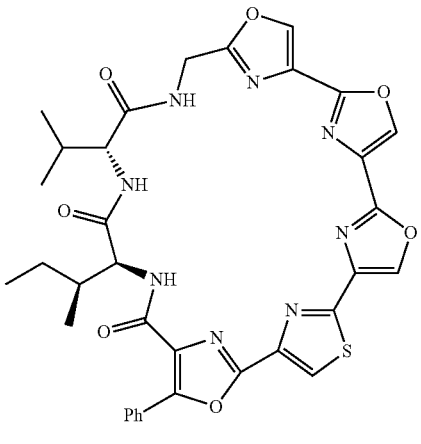

YM-216391

The mechanism of action of YM-216391 has not yet been elucidated.

Currently, there is a need for novel therapeutic agents and therapeutic methods that are useful for treating diseases such as cancer. Such agents may have improved binding affinity for G-quadruplex DNA and/or they may have advantageous drug-like properties.

SUMMARY OF THE INVENTION

The present invention provides compounds that exhibit anti-cancer properties. Accordingly, in one embodiment of the invention there is provided a compound of the invention which is compound of formula (I):

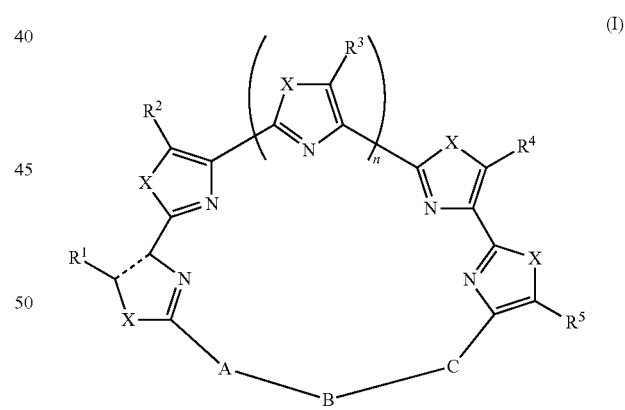

(I)

wherein:
the bond represented by ---- is a single or double bond;
A is (—C(=O)NH—CH(R)—)$_x$ or (—CH(R)—NH—C(=O)—)$_x$;
B is a group of formula:

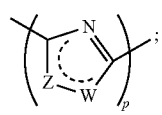

C is (—C(=O)NH—CH(R)—)$_y$ or (—CH(R)—NH—C(=O)—)$_y$;

n is 0, 1 or 2;
p is 0, 1, or 2;
x is 1 or 2;
y is 0, 1 or 2;
provided that the sum of n, p, x and y is 4;
X is O, S or NH;
one of W and Z is O, S or NH and the other of W and Z is CR$^6$;
each of R$^1$, R$^2$, R$^3$, R$^4$, R$^5$ and R$^6$ is independently hydrogen, (C$_1$-C$_6$)alkyl, (C$_1$-C$_6$)alkoxy, aryl or heteroaryl, wherein each (C$_1$-C$_6$)alkyl and (C$_1$-C$_6$)alkoxy is optionally substituted with OH, (C$_1$-C$_6$)alkoxy, (C$_1$-C$_6$)allylthio, aryl, NR$^7$R$^8$, or —C(=O)NR$^9$R$^{10}$; and wherein each aryl or heteroaryl is optionally substituted with one or two substituents selected independently from a halo, (C$_1$-C$_6$)alkyl, (C$_1$-C$_6$)alkoxy, NR$^7$R$^8$, and NR$^7$R$^8$(C$_1$-C$_6$)alkyl-;
each R is independently hydrogen, (C$_1$-C$_6$)alkyl, (C$_2$-C$_6$)alkenyl, (C$_1$-C$_6$)alkoxy, aryl or heteroaryl, wherein each (C$_1$-C$_6$)alkyl, (C$_2$-C$_6$)alkenyl and (C$_1$-C$_6$)alkoxy is optionally substituted with OH, (C$_1$-C$_6$)alkoxy, (C$_1$-C$_6$)alkylthio, aryl, NR$^{11}$R$^{12}$, or —C(=O)NR$^{13}$R$^{14}$; and wherein each aryl or heteroaryl is optionally substituted with one or two substituents selected independently from halo, (C$_1$-C$_6$)alkyl, NR$^{11}$R$^{12}$, and NR$^{13}$R$^{14}$(C$_1$-C$_6$)alkyl-;
each of R$^7$ and R$^8$ is independently hydrogen, (C$_1$-C$_6$)alkyl, (C$_1$-C$_6$)alkanoyl, arylcarbonyl, heteroarylcarbonyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^7$ and R$^8$ together with the nitrogen to which they are attached form a pyrrolidino, piperidino, piperazino, morpholino, thiomorpholino, or azepino ring; and
each of R$^9$ and R$^{10}$ is independently hydrogen, (C$_1$-C$_6$)alkyl, (C$_1$-C$_6$)alkanoyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^9$ and R$^{10}$ together with the nitrogen to which they are attached form a pyrrolidino, piperidino, piperazino, morpholino, thiomorpholino, or azepino ring;
each of R$^{11}$ and R$^{12}$ is independently hydrogen, (C$_1$-C$_6$)alkyl, (C$_1$-C$_6$)alkanoyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^{11}$ and R$^{12}$ together with the nitrogen to which they are attached form a pyrrolidino, piperidino, piperazino, morpholino, thiomorpholino, or azepino ring; and
each of R$^{13}$ and R$^{14}$ is independently hydrogen, (C$_1$-C$_6$)alkyl, (C$_1$-C$_6$)alkanoyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^{13}$ and R$^{14}$ together with the nitrogen to which they are attached form a pyrrolidino, piperidino, piperazino, morpholino, thiomorpholino, or azepino ring;
each of R$^{15}$ and R$^{16}$ is independently hydrogen, (C$_1$-C$_6$)alkyl, or (C$_1$-C$_6$)alkanoyl; or R$^{15}$ and R$^{16}$ together with the nitrogen to which they are attached form a pyrrolidino, piperidino, piperazino, morpholino, thiomorpholino, or azepino ring;
or a salt thereof.

In one embodiment of the invention the compound of formula (I) is not YM-216391.

In one embodiment the invention also provides a compound of formula (II) or (III):

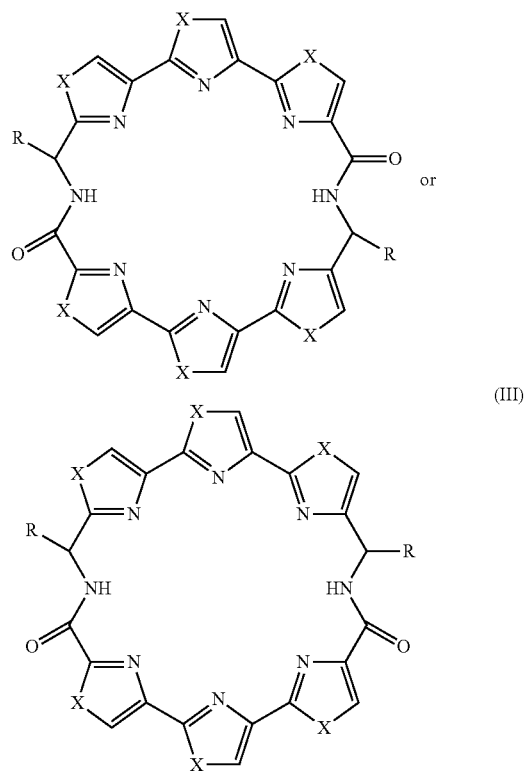

wherein:
each X is independently O, S or NH;
each R is independently hydrogen, (C$_1$-C$_6$)alkyl, (C$_2$-C$_6$)alkenyl, (C$_1$-C$_6$)alkoxy, aryl or heteroaryl, wherein each (C$_1$-C$_6$)alkyl, (C$_2$-C$_6$)alkenyl or (C$_1$-C$_6$)alkoxy is optionally substituted with OH, (C$_1$-C$_6$)alkoxy, (C$_1$-C$_6$)alkylthio, aryl, NR$^{11}$R$^{12}$; or —C(=O)NR$^{13}$R$^{14}$; and wherein each aryl or heteroaryl is optionally substituted with one or two substituents selected independently from halo, (C$_1$-C$_6$)alkyl, NR$^{11}$R$^{12}$; and NR$^{13}$R$^{14}$(C$_1$-C$_6$)alkyl-;
each of R$^{11}$ and R$^{12}$ is independently hydrogen, (C$_1$-C$_6$)alkyl, (C$_1$-C$_6$)alkanoyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^{11}$ and R$^{12}$ together with the nitrogen to which they are attached form a pyrrolidino, piperidino, piperazino, morpholino, thiomorpholino, or azepino ring; and
each of R$^{13}$ and R$^{14}$ is independently hydrogen, (C$_1$-C$_6$)alkyl, (C$_1$-C$_6$)alkanoyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^{13}$ and R$^{14}$ together with the nitrogen to which they are attached form a pyrrolidino, piperidino, piperazino, morpholino, thiomorpholino, or azepino ring;

each of R$^{15}$ and R$^{16}$ is independently hydrogen, (C$_1$-C$_6$) alkyl or (C$_1$-C$_6$)alkanoyl; or R$^{15}$ and R$^{16}$ together with the nitrogen to which they are attached form a pyrrolidino, piperidino, piperazino, morpholino, thiomorpholino, or azepino ring;

or a salt thereof.

The invention also provides a pharmaceutical composition comprising a compound of formula (I), (II), or (III) or a pharmaceutically acceptable salt thereof, in combination with a pharmaceutically acceptable diluent or carrier.

Additionally, the invention provides a therapeutic method for treating cancer comprising administering to a mammal (e.g., a human male or female) in need of such therapy, an effective amount of a compound of formula (I), (II), or (III), or a pharmaceutically acceptable salt thereof.

The invention also provides a compound of formula (I), (II), or (III) or a pharmaceutically acceptable salt thereof for use in medical therapy (e.g., for use in treating cancer), as well as the use of a compound of formula (I), (II), or (III) or a pharmaceutically acceptable salt thereof for the manufacture of a medicament useful for the treatment of cancer in a mammal, such as a human.

The invention also provides a compound of formula (I), (II), or (III), or a pharmaceutically acceptable salt thereof for use in the prophylactic or therapeutic treatment of cancer.

The invention also provides processes and intermediates disclosed herein that are useful for preparing compounds of formula (I), (II), or (III) or salts thereof.

DETAILED DESCRIPTION

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl denotes an aromatic heterocyclic ring containing 5 or 6-ring members including from one to four ring hetero atoms selected from oxygen, sulfur and nitrogen, the remainder being carbon, which ring is optionally ortho-fused to a benzene ring or another 5- or 6-membered heteroaromatic ring.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed below for radicals, substituents, and ranges, are for illustration only; they do not exclude other defined values or other values within defined ranges for the radicals and substituents.

Specifically, (C$_1$-C$_6$)alkyl can be methyl, ethyl, propyl, isopropyl, butyl, iso-butyl, sec-butyl, pentyl, 3-pentyl, or hexyl; (C$_2$-C$_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; (C$_1$-C$_6$)alkanoyl can be acetyl, propanoyl or butanoyl; (C$_1$-C$_6$)alkoxy can be methoxy, ethoxy, propoxy, isopropoxy, butoxy, iso-butoxy, sec-butoxy, pentoxy, 3-pentoxy, or hexyloxy; and aryl can be phenyl, indenyl, or naphthyl. Aryl can be phenyl. Heteroaryl can be pyridyl.

An example of the bond represented by ---- is a double bond.

In one embodiment, the compound of formula (I) is a compound of formula (I')

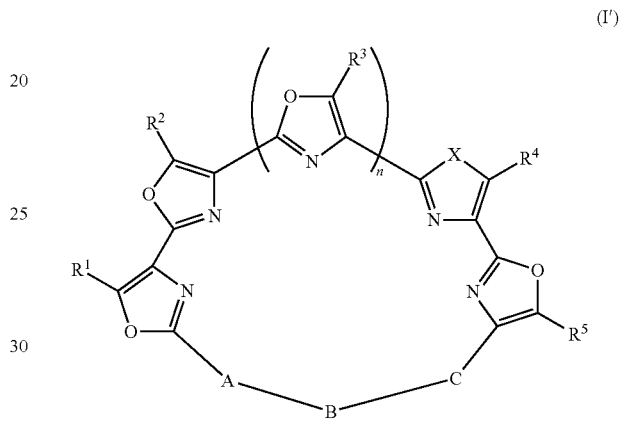

(I')

An example of a particular value for each X in the compounds of formulae (I) and (I') is O.

Examples for each group of formula —C(=O)NH—CH(R)— are residues of D- or L-amino acids, such as D- or L-glycine, alanine, valine, leucine, isoleucine and phenylalanine, more particularly alanine, valine, leucine, isoleucine, and phenylalanine.

Examples of particular values for R are independently hydrogen, methyl, isopropyl, 1-methylpropyl, 2-methylpropyl and benzyl, more particularly methyl, isopropyl, 1-methylpropyl, 2-methylpropyl and benzyl.

Examples of particular values for R are independently (C$_1$-C$_6$)alkyl or (C$_2$-C$_6$)alkenyl wherein each (C$_1$-C$_6$)alkyl, and (C$_2$-C$_6$)alkenyl, is optionally substituted with NR$^{11}$R$^{12}$.

Examples of particular values for R are independently aminomethyl, 2-aminoethyl, 3-aminopropyl or 4-aminobutyl.

A particular value for R$^1$ is hydrogen.

A particular value for R$^2$ is hydrogen.

A particular value for R$^3$ is hydrogen or —(CH$_2$)$_q$—NR$^a$R$^b$ in which q is 1, 2, 3 or 4, R$^a$ is hydrogen and R$^b$ is acetyl, benzoyl, pyridylcarbonyl, methoxycarbonyl, N-methylaminocarbonyl or phenyl.

A particular value for R$^4$ is hydrogen.

A particular value for R$^5$ is hydrogen; methyl, phenyl, N-methylaminophenyl, N-acetylaminoethylphenyl, pyridyl, or methoxypyridyl.

A particular value for R$^6$ is hydrogen.

A particular value for A is —C(=O)NH—CH(R)—.

A particular value for A is —C(=O)NH—CH(R)—C(=O)NH—CH(R)—.

A particular value for A is —C(=O)NH—CH$_2$—.

A particular value for A is —C(=O)NH—CH₂—C(=O)NH—CH₂—.
A particular value for A is —CH(R)—NH—C(=O)—.
A particular value for A is —CH(R)—NH—C(=O)—CH(R)—NH—C(=O)—.
A particular value for A is —CH₂—NH—C(=O)—.
A particular value for A is —CH₂NH—C(=O)—CH₂—NH—C(=O)—.
A specific compound of formula (I) is:
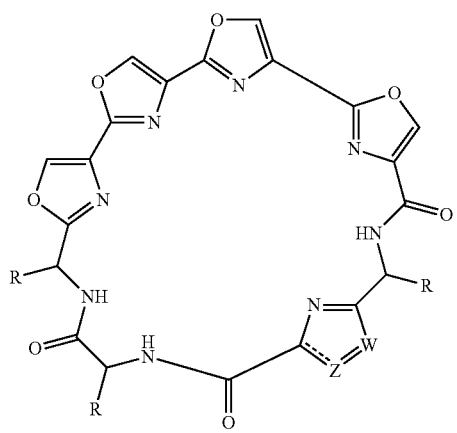
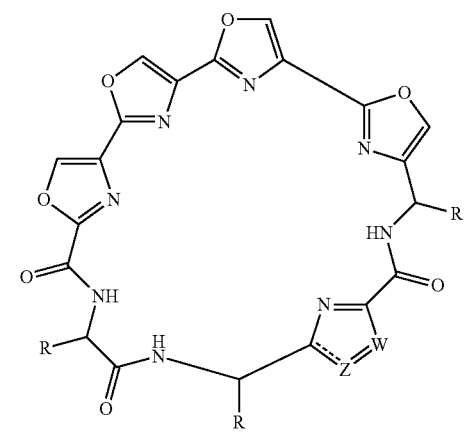
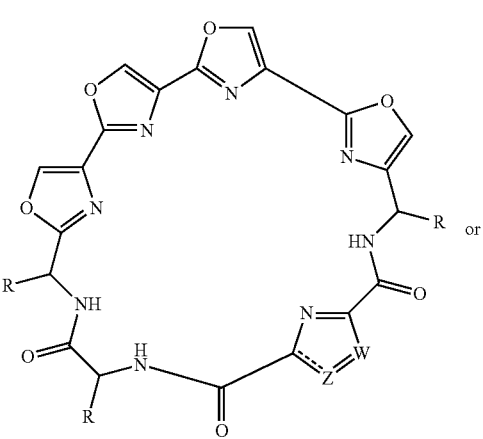
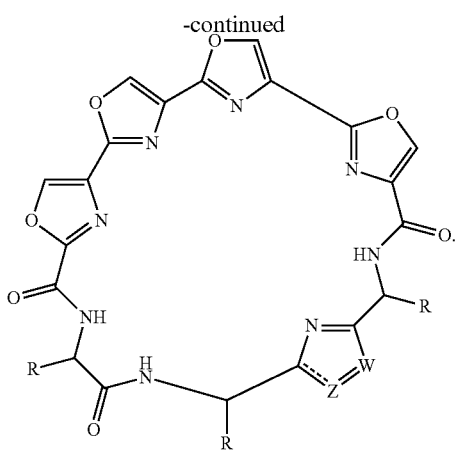
A specific compound of formula (I) is:
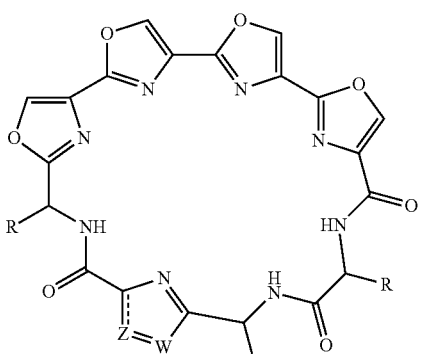
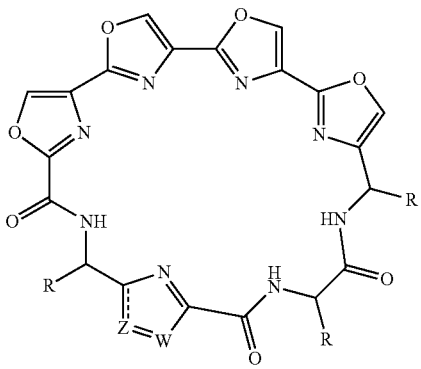
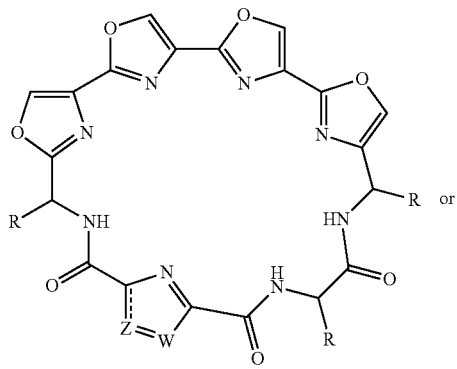

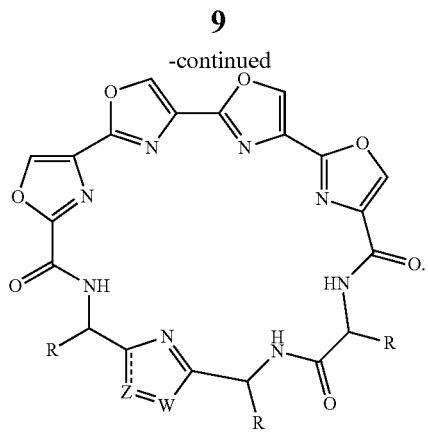
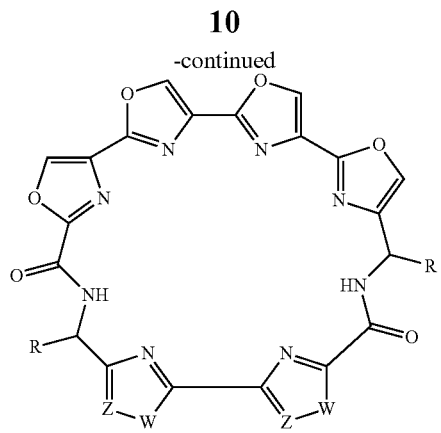
A specific compound of formula (I) is:
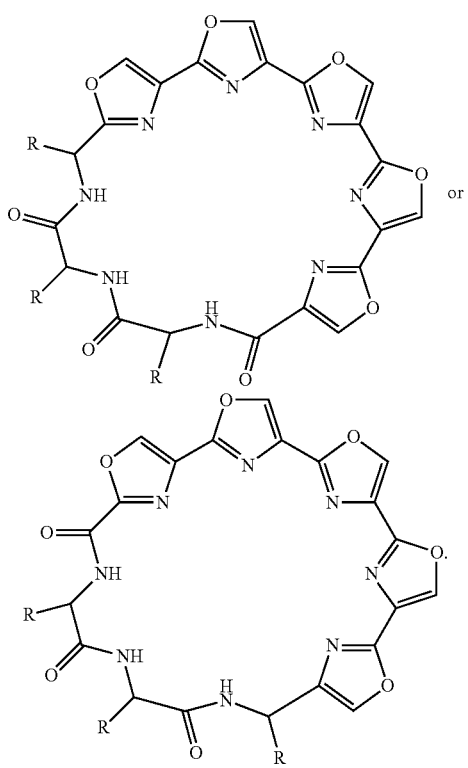
A specific compound of formula (I) is:
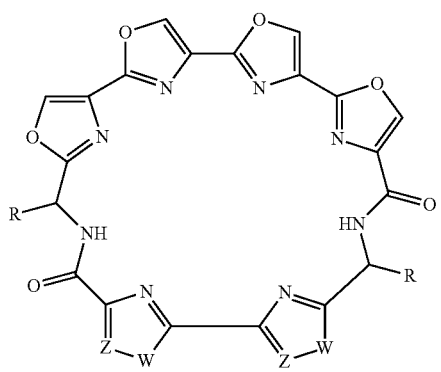
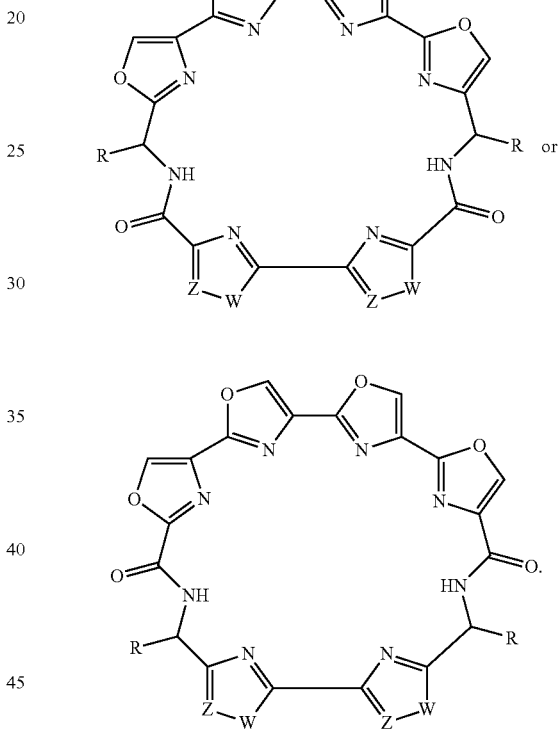
A specific compound of formula (I) is:
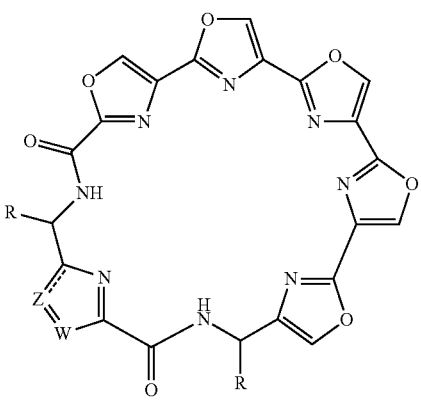

-continued

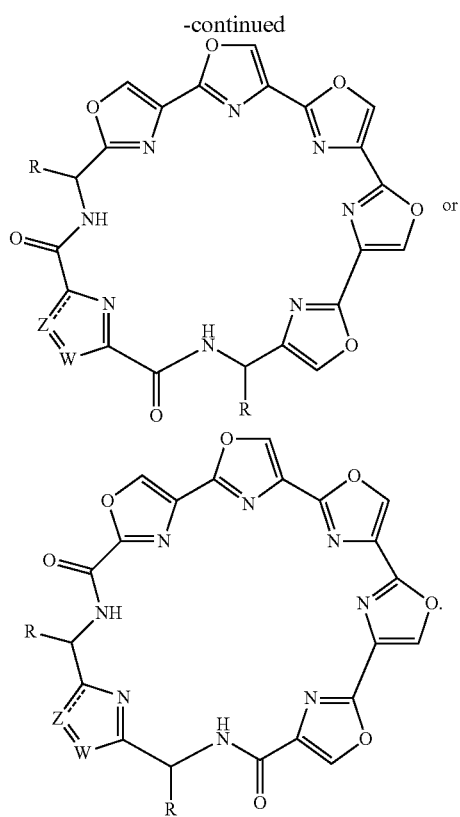

A specific compound of formula (I) is:

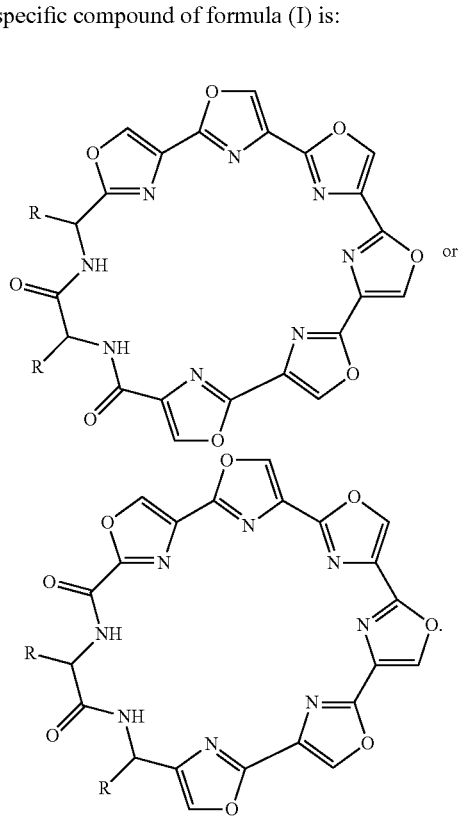

A specific group of compounds are compounds wherein W is O or S and Z is $CR^6$.

A specific group of compounds are compounds wherein Z is O or S and W is $CR^6$.

In one embodiment of the invention the compound of formula (I) is not a compound of the following formula:

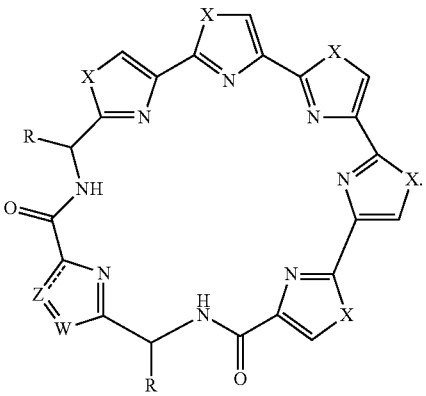

In one embodiment of the invention the compound of formula (I) is not a compound of the following formula:

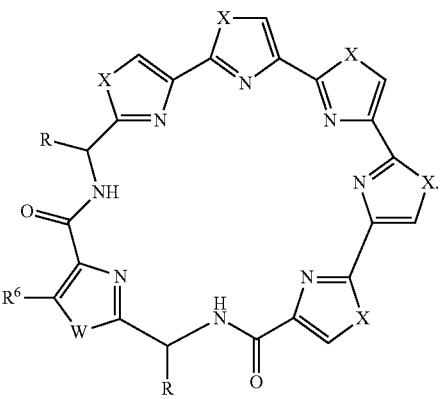

Representative examples of compounds of formula (I) are compounds of formula:

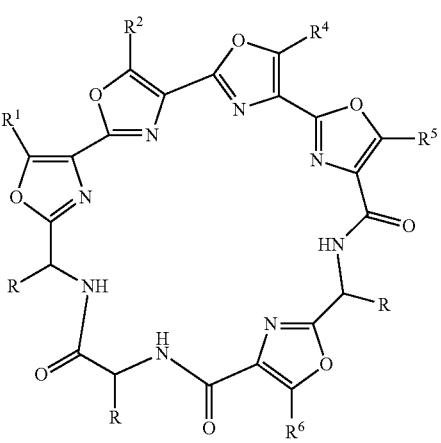

(Ia)

(Ib)
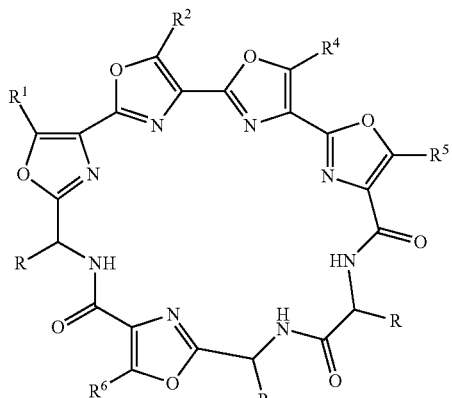
(Ie)
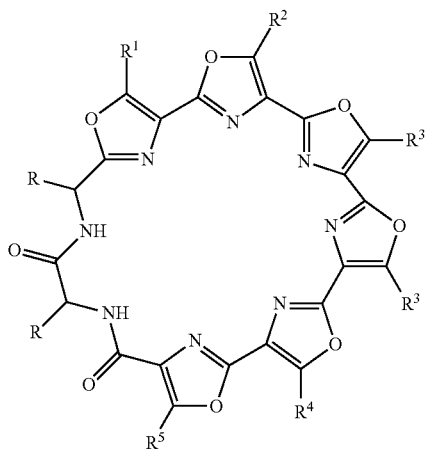
(Ic)
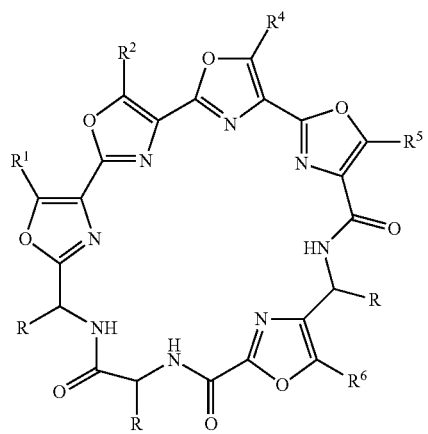
(If)
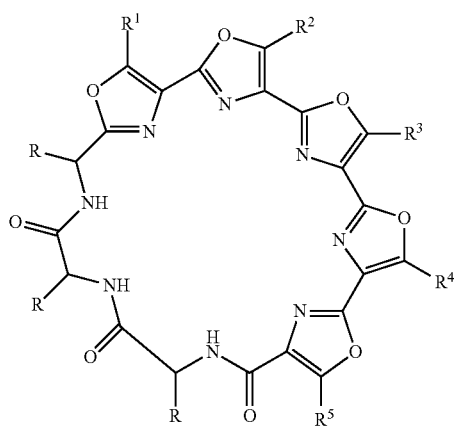
(Id)
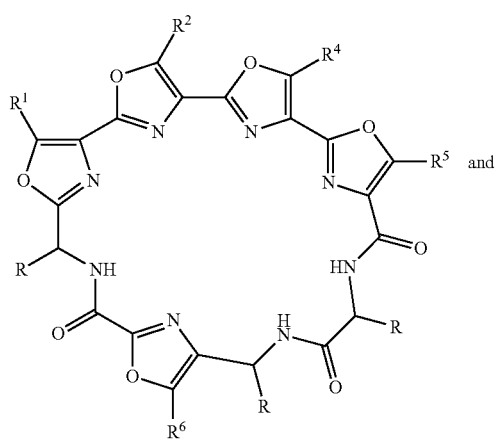
(Ig)

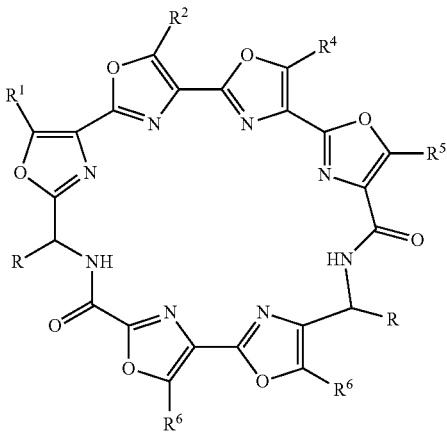

(Ih)

In one embodiment the invention provides a compound of formula (I) wherein x is 1, y is 0 and n+p is 1, 2 or 4 and wherein x is 1, y is 1, p is 1 and n is 0 or 2.

In one embodiment the invention provides a compound of formula (I) wherein x is 1, y is 0 and n+p is 1, 2 or 4.

In one embodiment the invention provides a compound of formula (I) wherein x is 1, y is 1, p is 1 and n is 0 or 2.

In one embodiment of the invention there is provided a compound of the invention which is compound of formula (I):

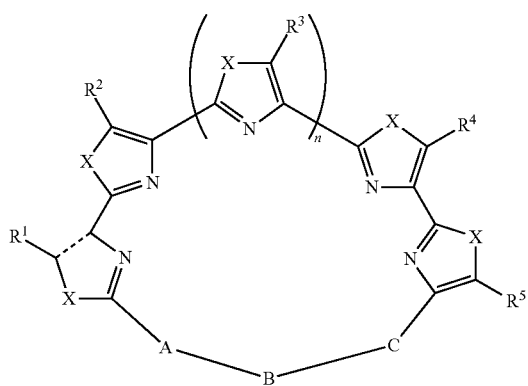

(I)

wherein:
the bond represented by ---- is a single or double bond;
A is (—C(=O)NH—CH(R)—)$_x$ or (—CH(R)—NH—C(=O)—)$_x$;
B is a group of formula:

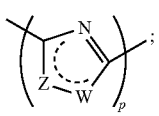

C is (—C(=O)NH—CH(R)—)$_y$ or (—CH(R)—NH—C(=O)—)$_y$;
n is 0, 1 or 2;
p is 0, 1, or 2;
x is 1 or 2;
y is 0, 1 or 2;
provided that the sum of n, p, x and y is 4;

X is O, S or NH;
one of W and Z is O, S or NH and the other of W and Z is CR$^6$;
each of R$^1$, R$^2$, R$^3$, R$^4$, R$^5$ and R$^6$ is independently hydrogen, (C$_1$-C$_6$)alkyl, (C$_1$-C$_6$)alkoxy, aryl, or heteroaryl, wherein each (C$_1$-C$_6$)alkyl and (C$_3$-C$_6$)alkoxy is optionally substituted with OH, (C$_1$-C$_6$)alkoxy, (C$_1$-C$_6$)alkylthio, aryl, NR$^7$R$^8$, or —C(=O)NR$^9$R$^{10}$; and wherein each aryl or heteroaryl is optionally substituted with one or two substituents selected independently from a halo, (C$_1$-C$_6$)alkyl, NR$^7$R$^8$, and NR$^7$R$^8$(C$_1$-C$_6$)alkyl-;

each R is independently hydrogen, (C$_1$-C$_6$)alkyl, (C$_1$-C$_6$)alkoxy, aryl, or heteroaryl, wherein each (C$_1$-C$_6$)alkyl and (C$_1$-C$_6$)alkoxy is optionally substituted with OH, (C$_1$-C$_6$)alkoxy, (C$_1$-C$_6$)alkylthio, aryl, NR$^{11}$R$^{12}$, or —C(=O)NR$^{13}$R$^{14}$; and wherein each aryl or heteroaryl is optionally substituted with one or two substituents selected independently from halo, (C$_1$-C$_6$)alkyl, NR$^{11}$R$^{12}$, and NR$^{13}$R$^{14}$(C$_1$-C$_6$)alkyl-;

each of R$^7$ and R$^8$ is independently hydrogen, (C$_1$-C$_6$)alkyl, (C$_1$-C$_6$)alkanoyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^7$ and R$^8$ together with the nitrogen to which they are attached form a pyrrolidino, piperidino, piperazino, morpholino, thiomorpholino, or azepino ring; and each of R$^9$ and R$^{10}$ is independently hydrogen, (C$_1$-C$_6$)alkyl, (C$_1$-C$_6$)alkanoyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^9$ and R$^{10}$ together with the nitrogen to which they are attached form a pyrrolidino, piperidino, piperazino, morpholino, thiomorpholino, or azepino ring;

each of R$^{11}$ and R$^{12}$ is independently hydrogen, (C$_1$-C$_6$)alkyl, (C$_1$-C$_6$)alkanoyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^{11}$ and R$^{12}$ together with the nitrogen to which they are attached form a pyrrolidino, piperidino, piperazino, morpholino, thiomorpholino, or azepino ring; and each of R$^{13}$ and R$^{14}$ is independently hydrogen, (C$_1$-C$_6$)alkyl, (C$_1$-C$_6$)alkanoyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^{13}$ and R$^{14}$ together with the nitrogen to which they are attached form a pyrrolidino, piperidino, piperazino, morpholino, thiomorpholino, or azepino ring;

each of R$^{15}$ and R$^{16}$ is independently hydrogen, (C$_1$-C$_6$)alkyl, or (C$_1$-C$_6$)alkanoyl; or R$^{15}$ and R$^{16}$ together with the nitrogen to which they are attached form a pyrrolidino, piperidino, piperazino, morpholino, thiomorpholino, or azepino ring;

or a salt thereof.

In one embodiment the invention also provides a compound of formula (II) or (III):

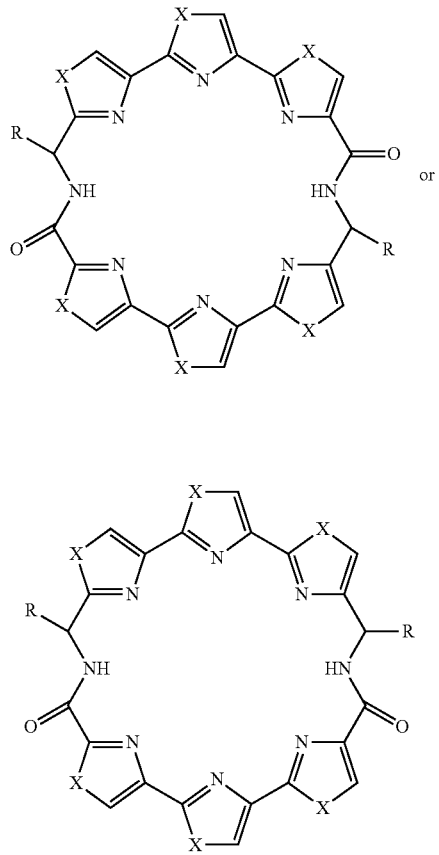

wherein:
each X is independently O, S or NH;
each R is independently hydrogen, $(C_1-C_6)$alkyl, $(C_1-C_6)$alkoxy, aryl or heteroaryl, wherein each $(C_1-C_6)$alkyl and $(C_1-C_6)$alkoxy is optionally substituted with OH, $(C_1-C_6)$alkoxy, $(C_1-C_6)$alkylthio, aryl, $NR^{11}R^{12}$ or —C(=O)$NR^{13}R^{14}$; and wherein each aryl or heteroaryl is optionally substituted with one or two substituents selected independently from halo, $(C_1-C_6)$alkyl, $NR^{11}R^{12}$, and $NR^{13}R^{14}(C_1-C_6)$alkyl-;
each of $R^{11}$ and $R^{12}$ is independently hydrogen, $(C_1-C_6)$alkyl, $(C_1-C_6)$alkanoyl, $(C_1-C_6)$alkoxycarbonyl, carbamoyl, N—$(C_1-C_6)$allylaminocarbonyl, aryl or heteroaryl, wherein each $(C_1-C_6)$alkyl, $(C_1-C_6)$alkanoyl, or $(C_1-C_6)$alkoxycarbony is optionally substituted with one or more $NR^{15}R^{16}$; or $R^{11}$ and $R^{12}$ together with the nitrogen to which they are attached form a pyrrolidino, piperidino, piperazino, morpholino, thiomorpholino, or azepino ring;
each of $R^{13}$ and $R^{14}$ is independently hydrogen, $(C_1-C_6)$alkyl, $(C_1-C_6)$alkanoyl, $(C_1-C_6)$alkoxycarbonyl, carbamoyl, N—$(C_1-C_6)$alkylaminocarbonyl, aryl or heteroaryl, wherein each $(C_1-C_6)$alkyl, $(C_1-C_6)$alkanoyl, or $(C_1-C_6)$alkoxycarbony is optionally substituted with one or more $NR^{15}R^{16}$; or $R^{13}$ and $R^{14}$ together with the nitrogen to which they are attached form a pyrrolidino, piperidino, piperazino, morpholino, thiomorpholino, or azepino ring; and
each of $R^{15}$ and $R^{16}$ is independently hydrogen, $(C_1-C_6)$alkyl, or $(C_1-C_6)$alkanoyl; or $R^{15}$ and $R^{16}$ together with the nitrogen to which they are attached form a pyrrolidino, piperidino, piperazino, morpholino, thiomorpholino, or azepino ring;
or a salt thereof.

The compounds of formula (I) can be prepared by forming an intermediate comprising a linear chain of the requisite polyazoles and aminoacids, or a protective derivative thereof, then cyclizing this by forming an amide bond and optionally removing any protecting groups and/or forming a salt.

Examples of synthetic routes to compounds of formula (I) are provided in Schemes 1 to 15 below.

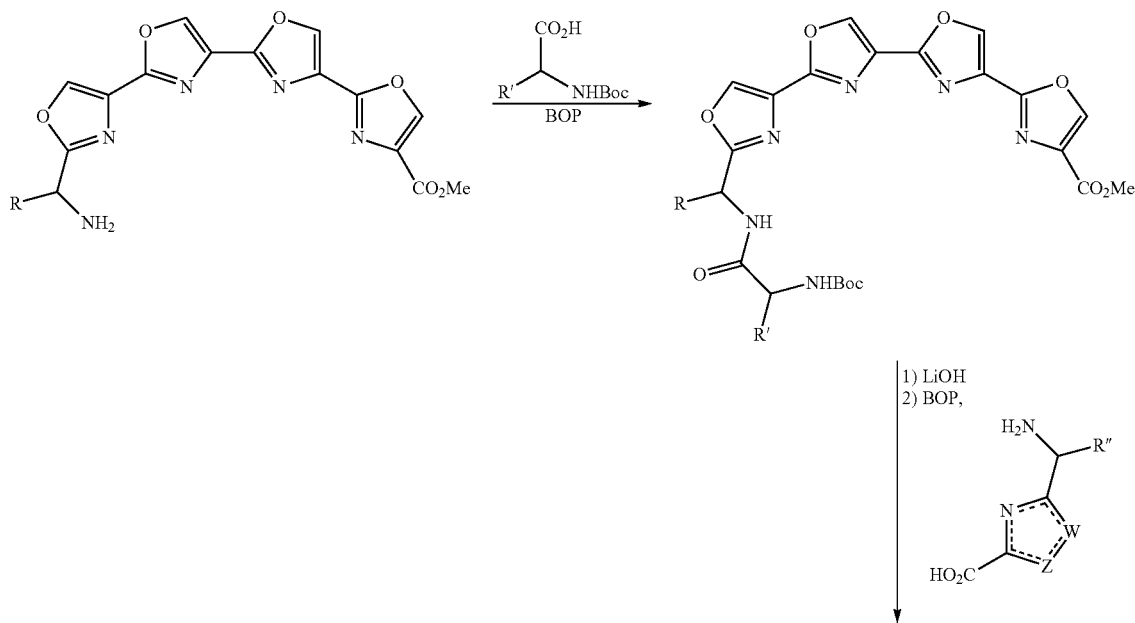

Scheme 1

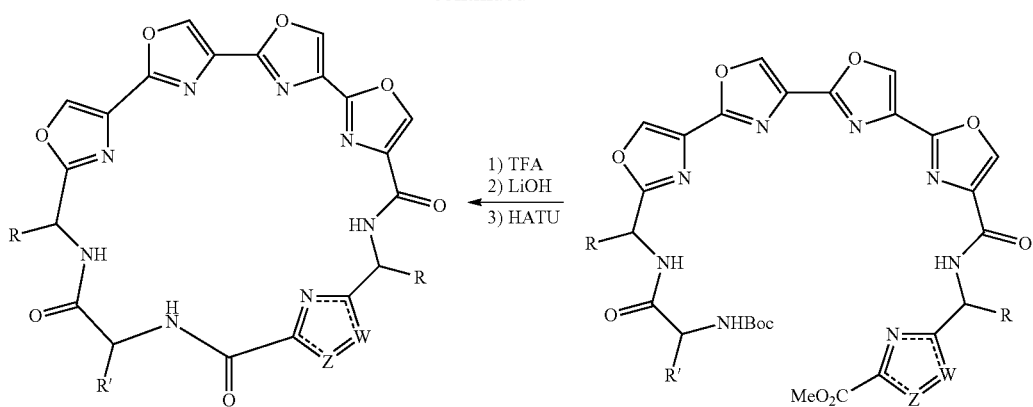
Where W = O, When Z = CH and W = CH, When Z = O
Scheme 2
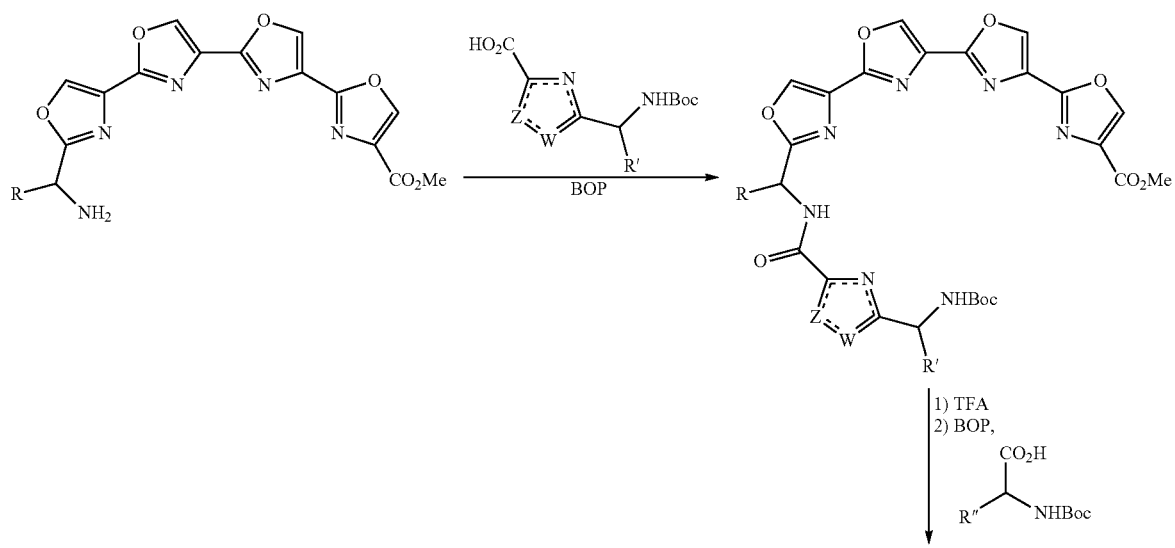
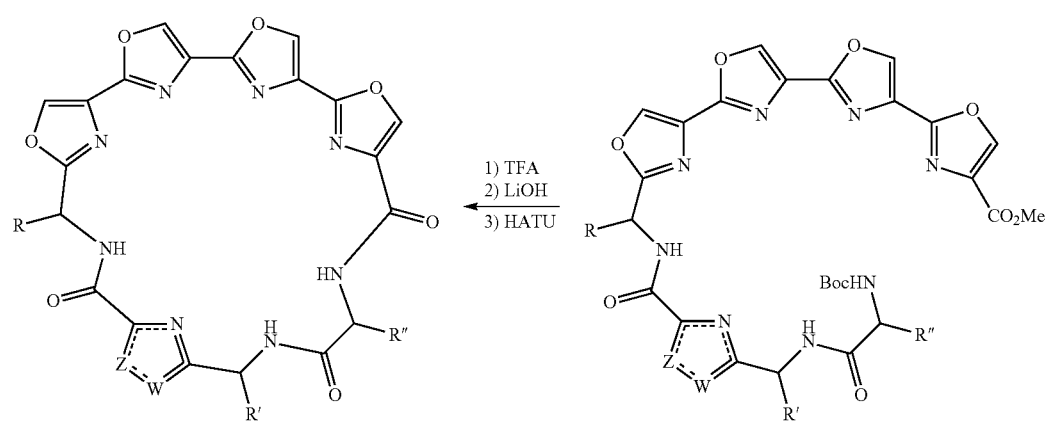
Where W = O, When Z = CH and W = CH, When Z = O Scheme 3
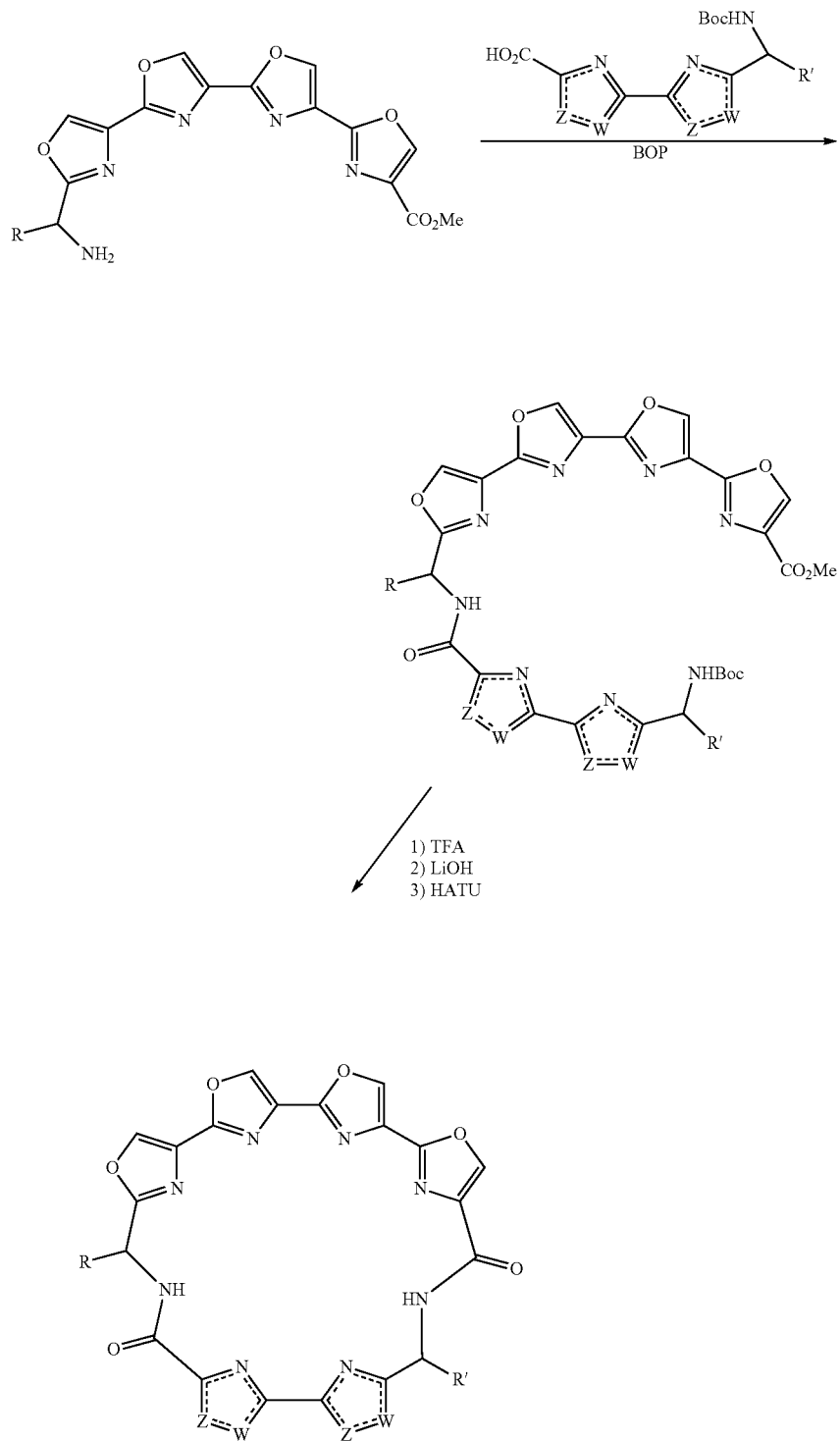
Where W = O, When Z = CH and W = CH, When Z = O Scheme 4
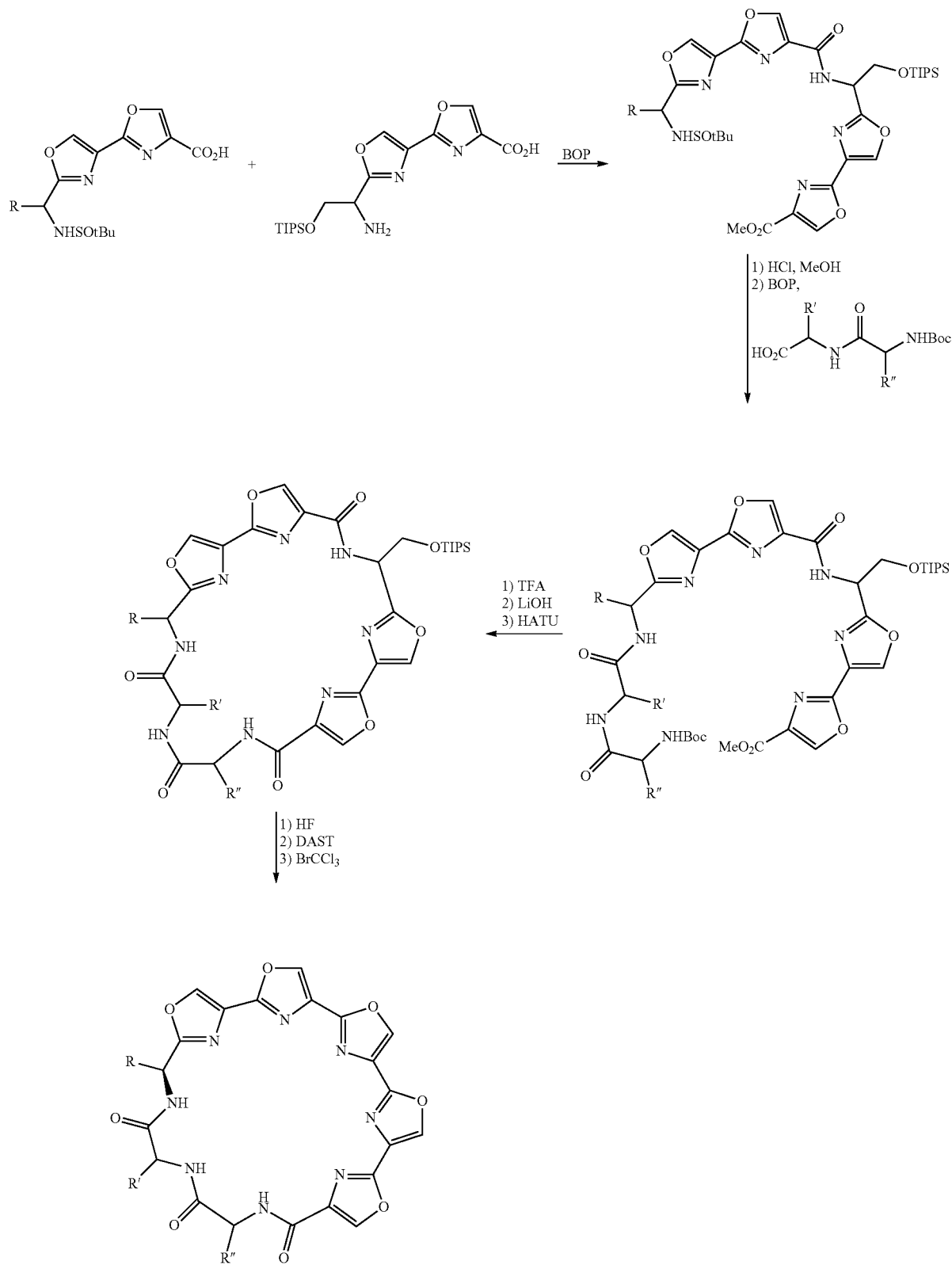

Scheme 5
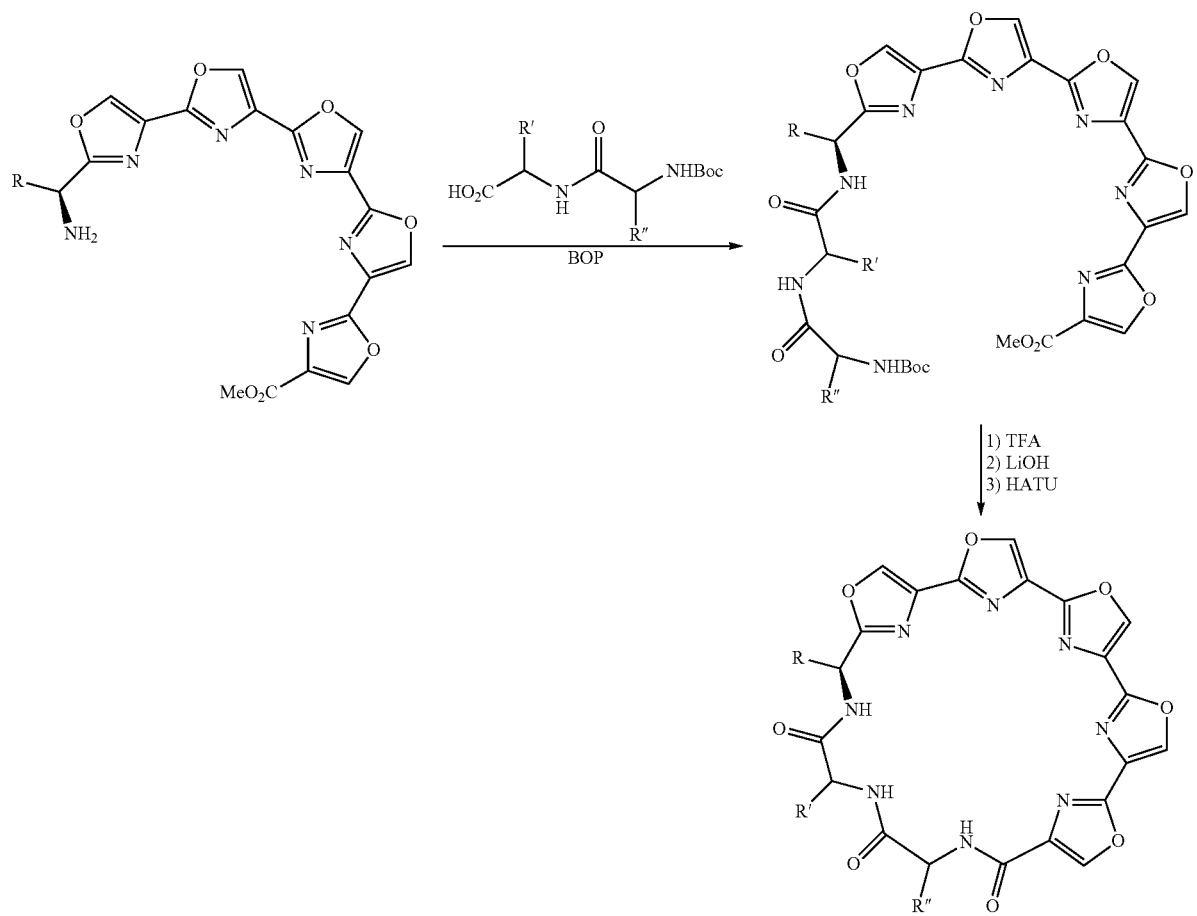
Scheme 6
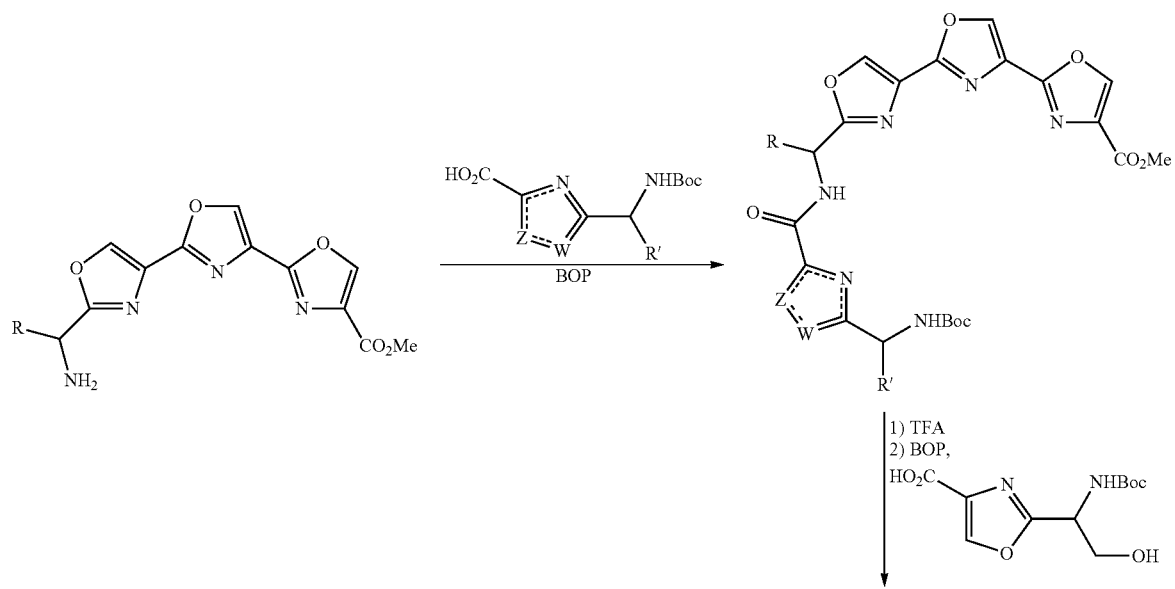

27    28
-continued
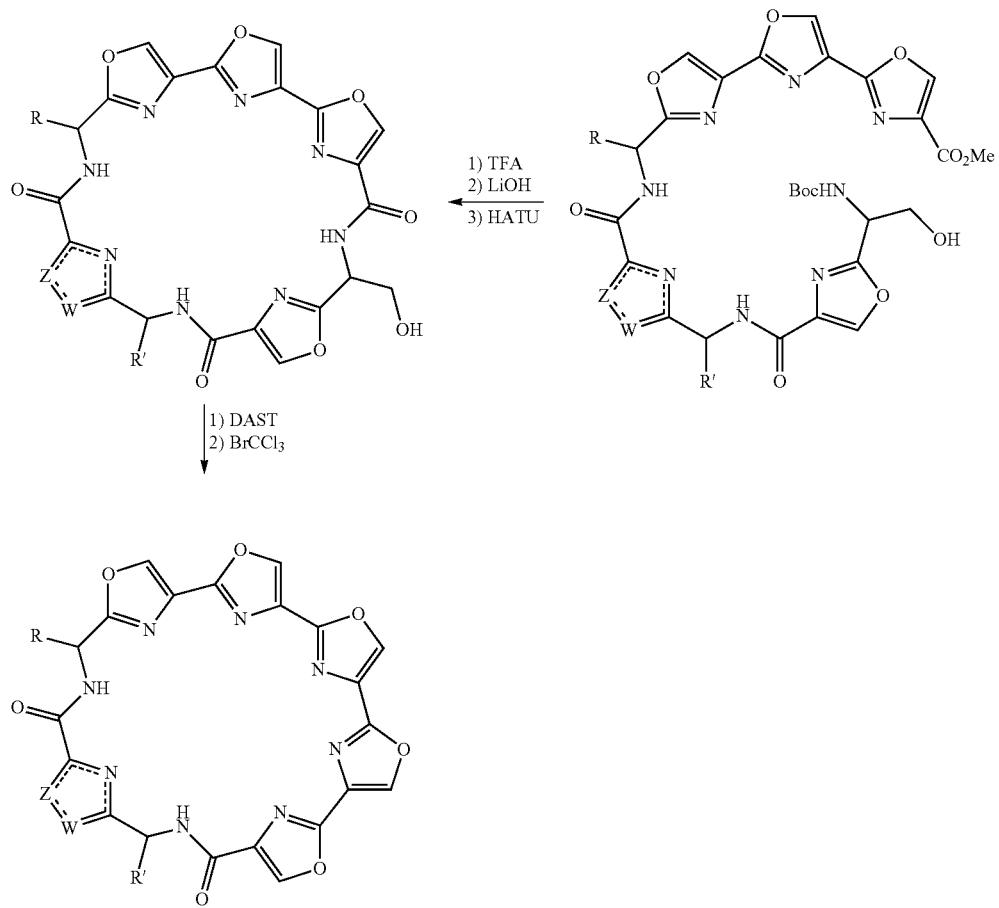
Where W = O, When Z = CH and W = CH, When Z = O
Scheme 7
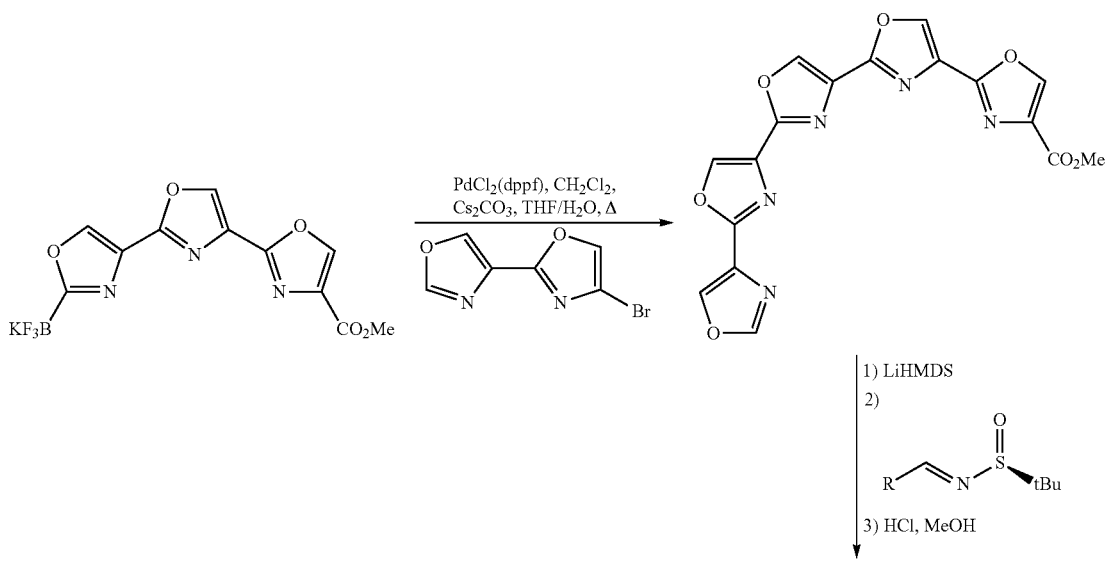

29 30
-continued
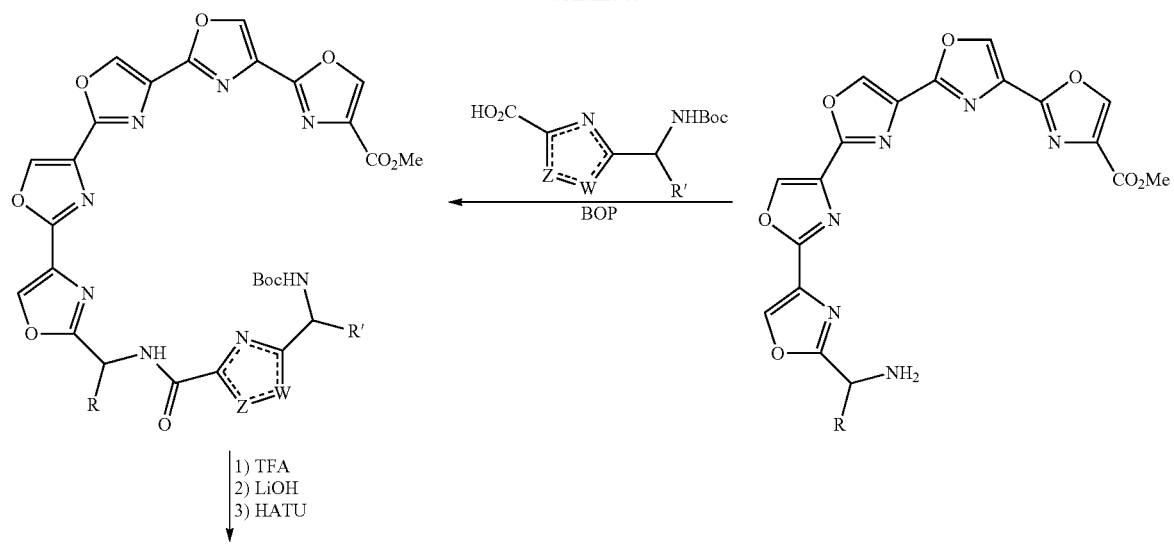
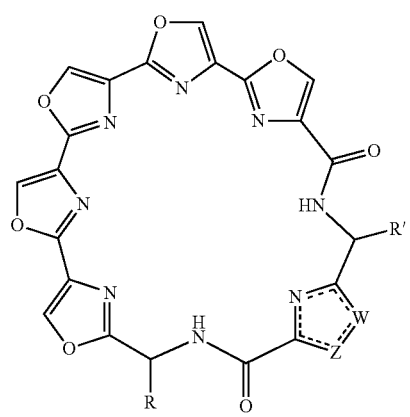
Where W = O, When Z = CH and W = CH, When Z = O
Scheme 8
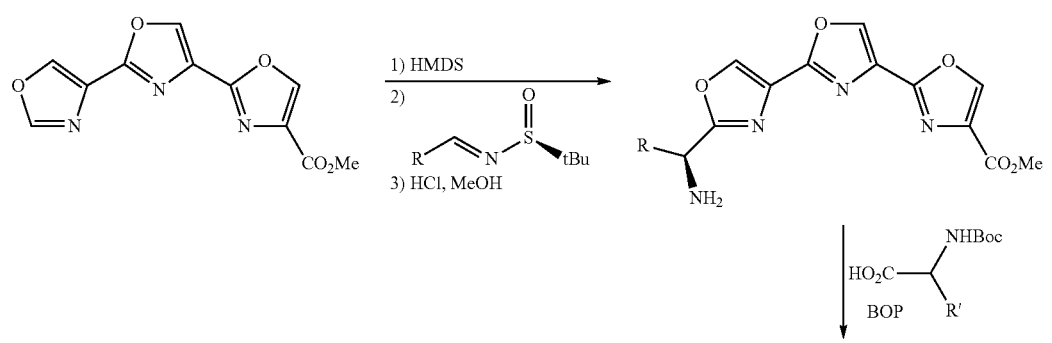

-continued
31
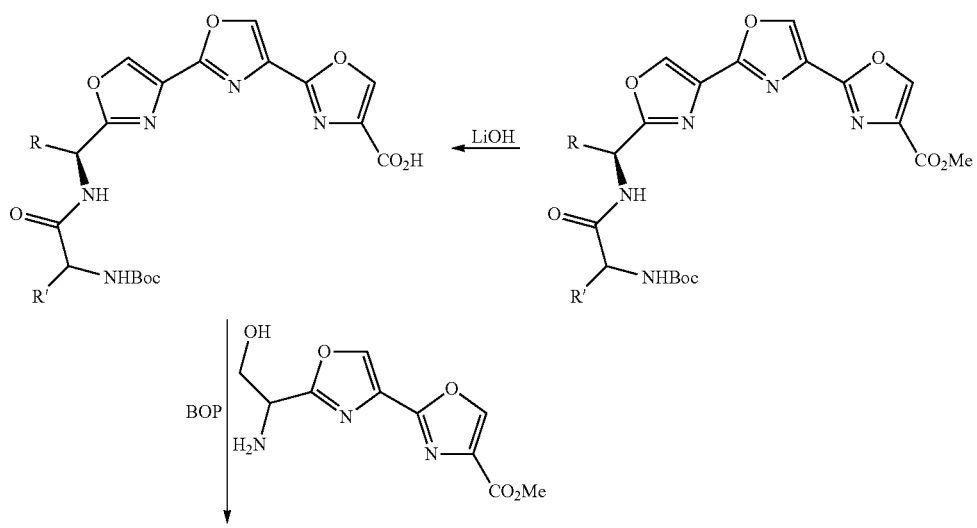
32
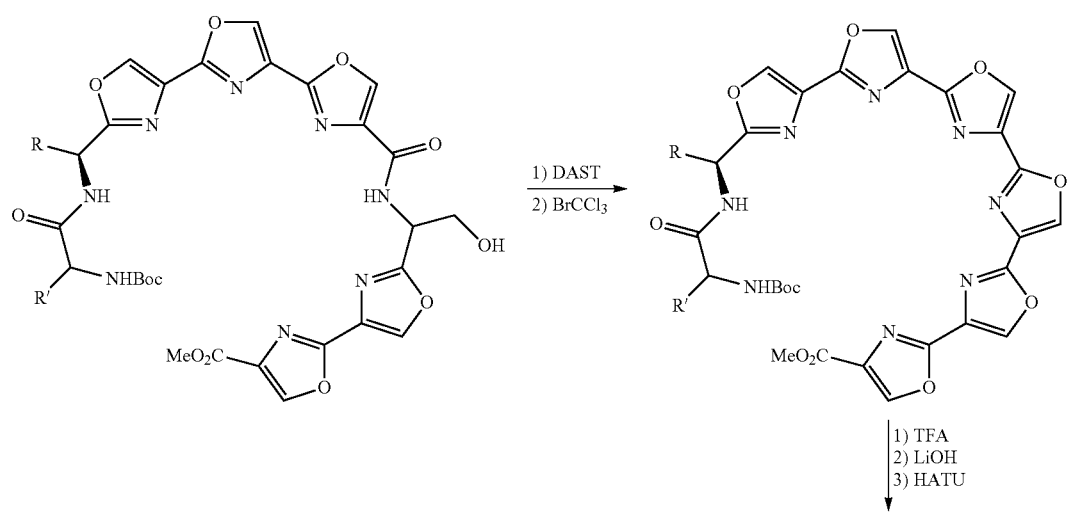
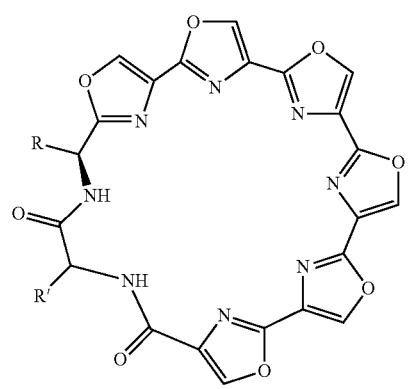

Scheme 9
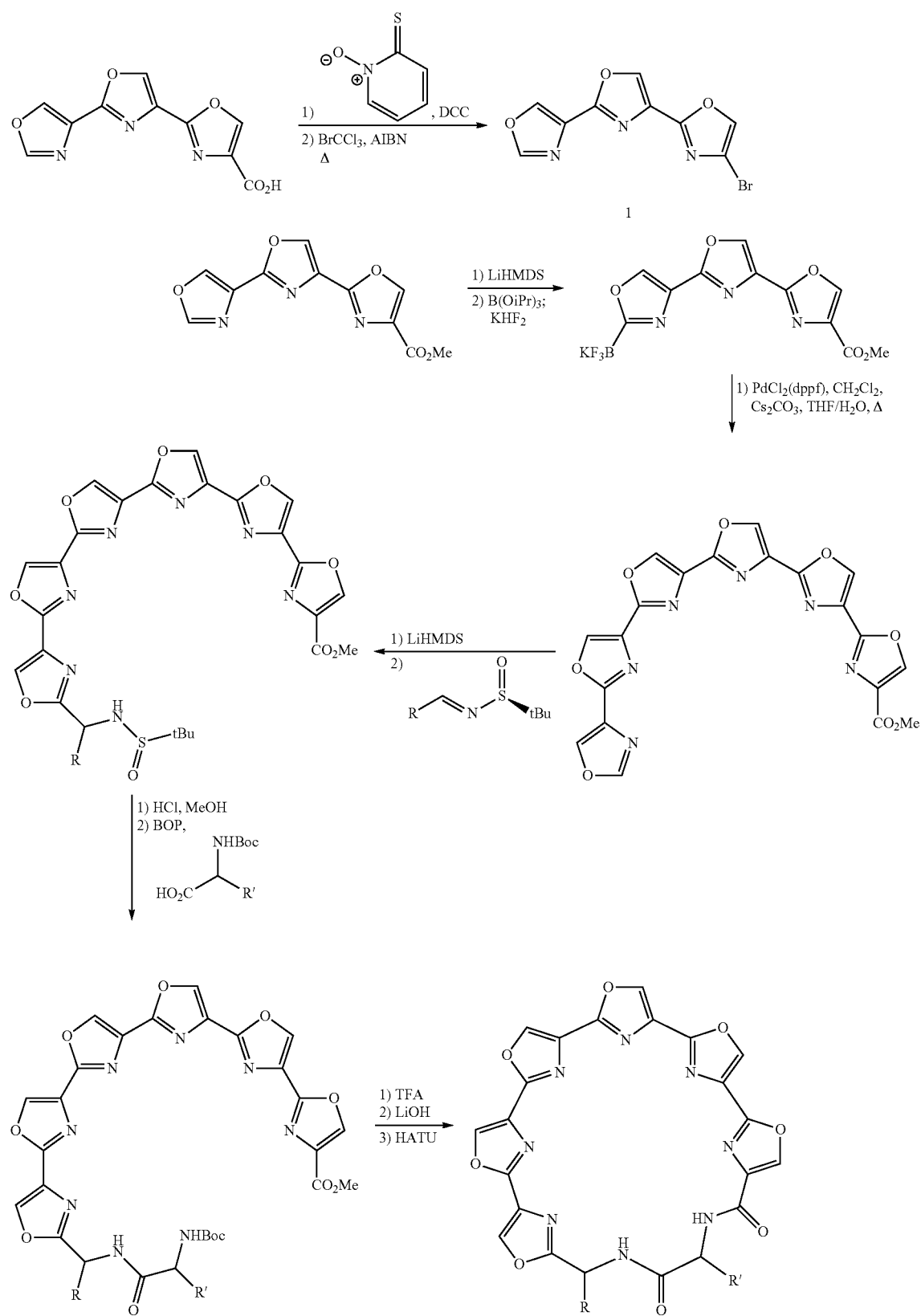

Scheme 10
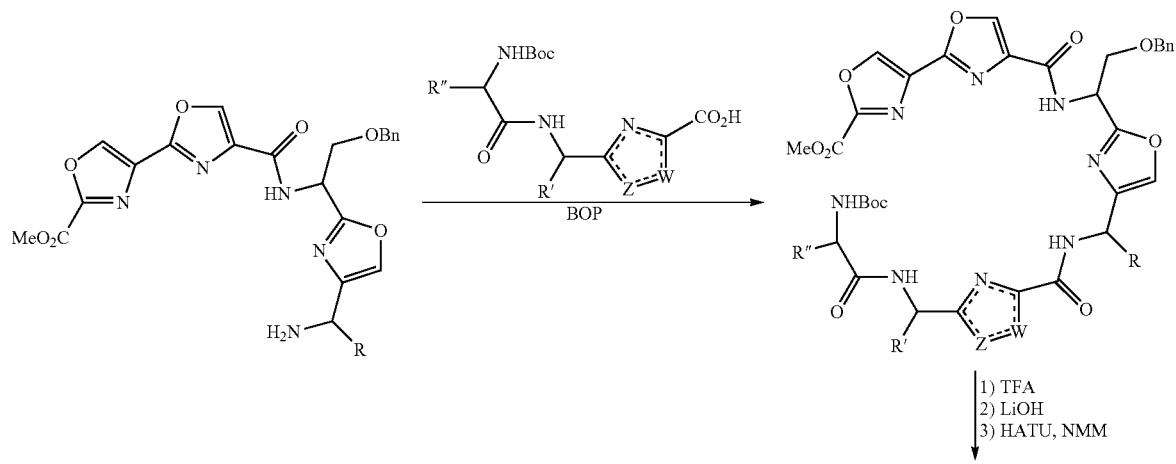
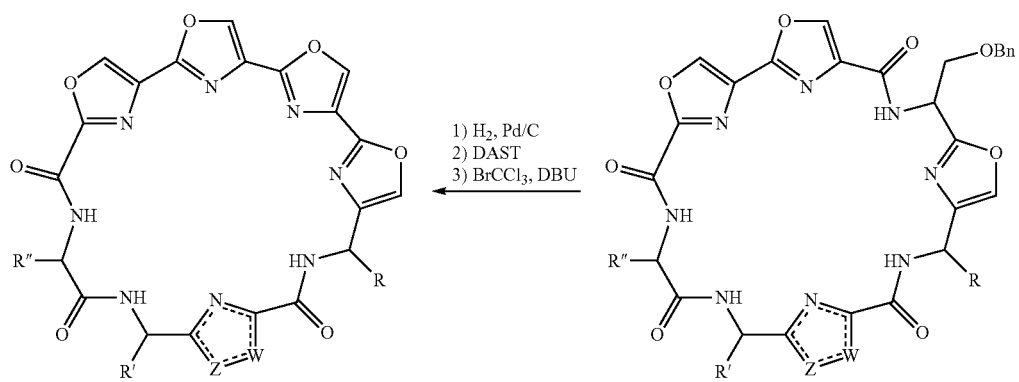
Scheme 11
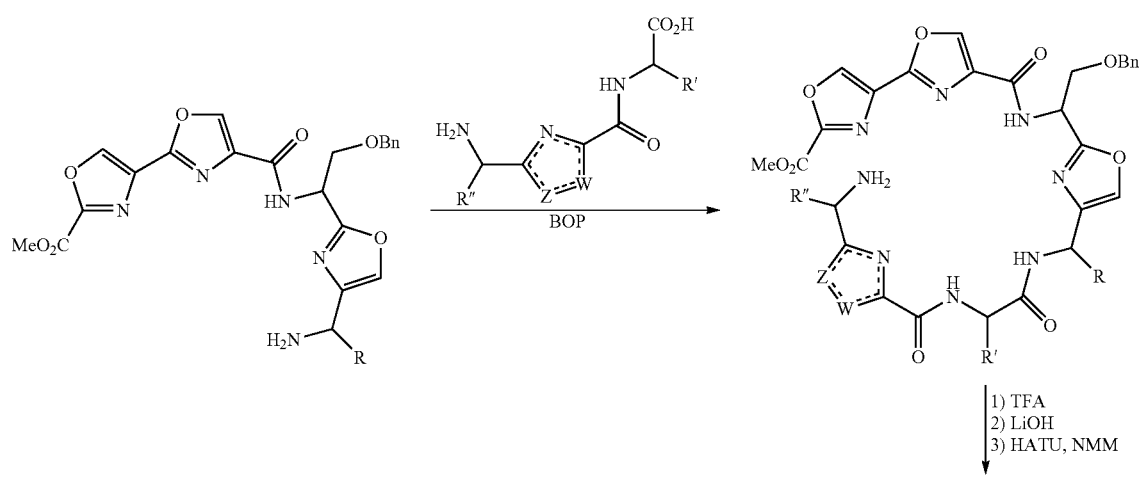

-continued
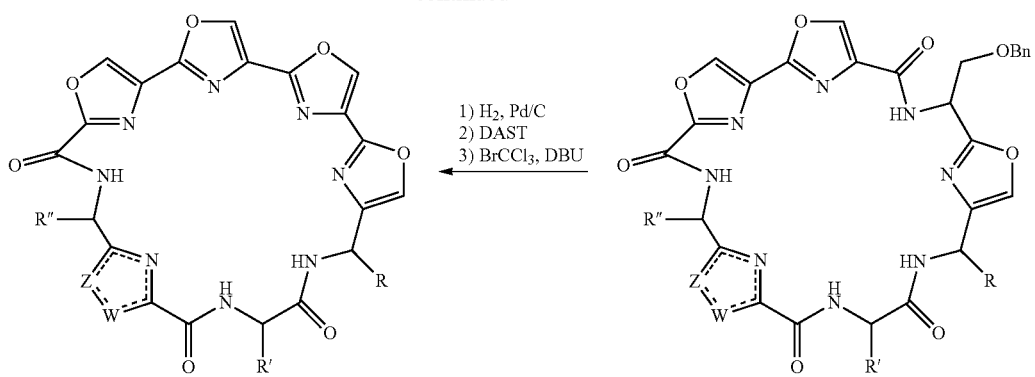
Scheme 12
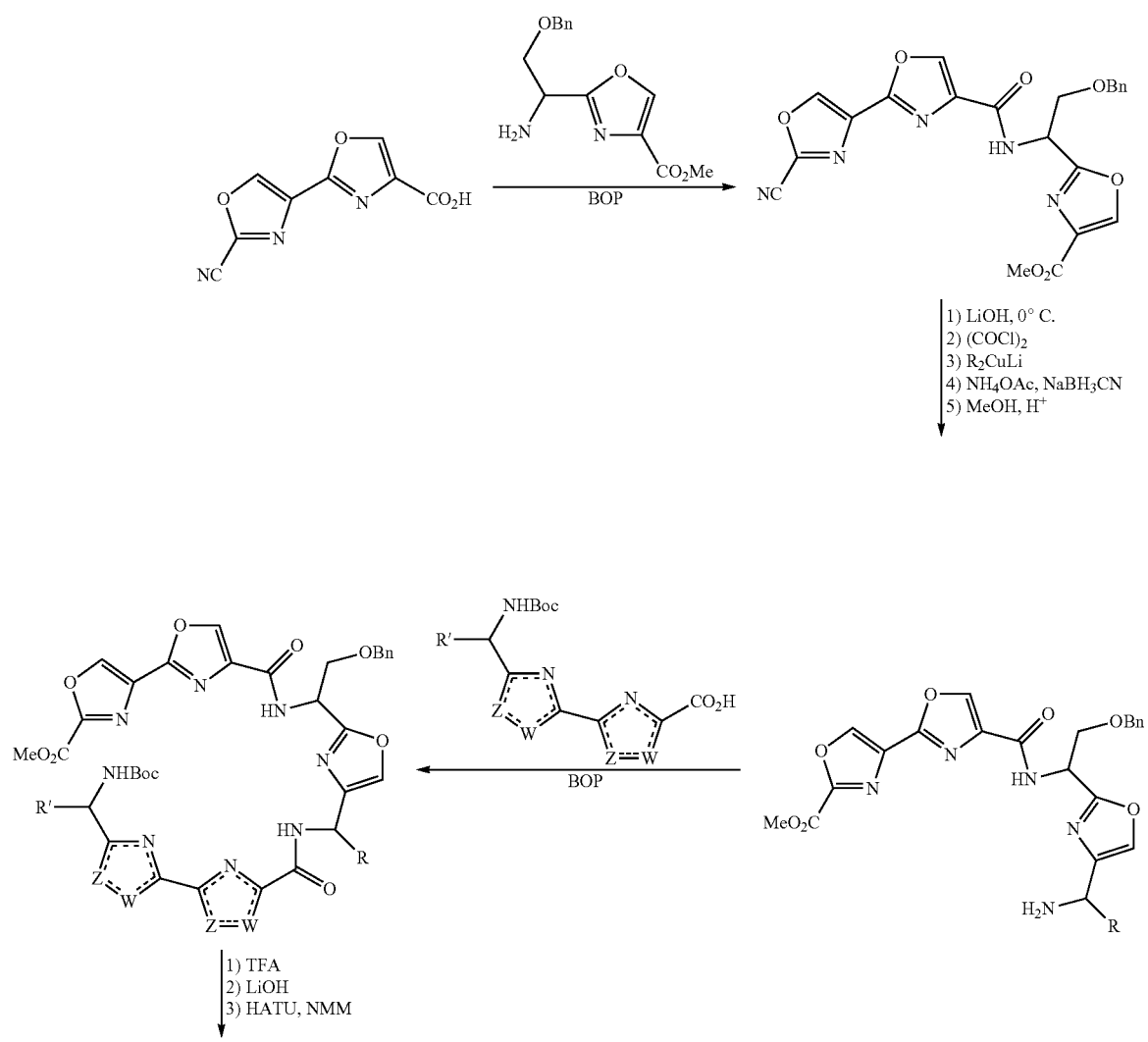

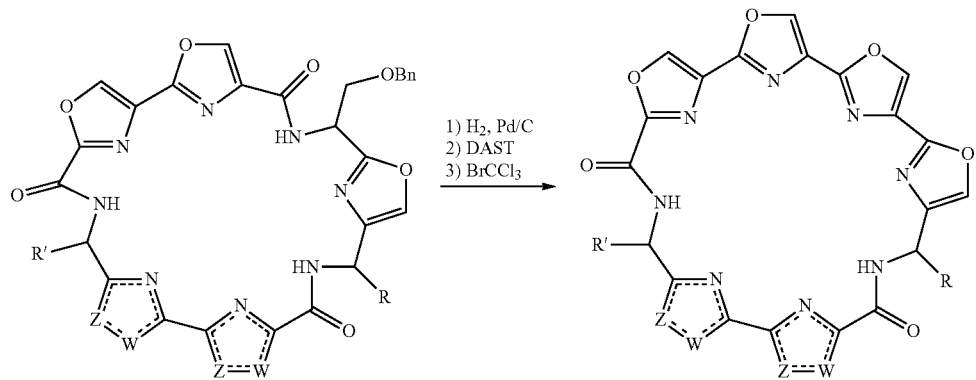
Scheme 13
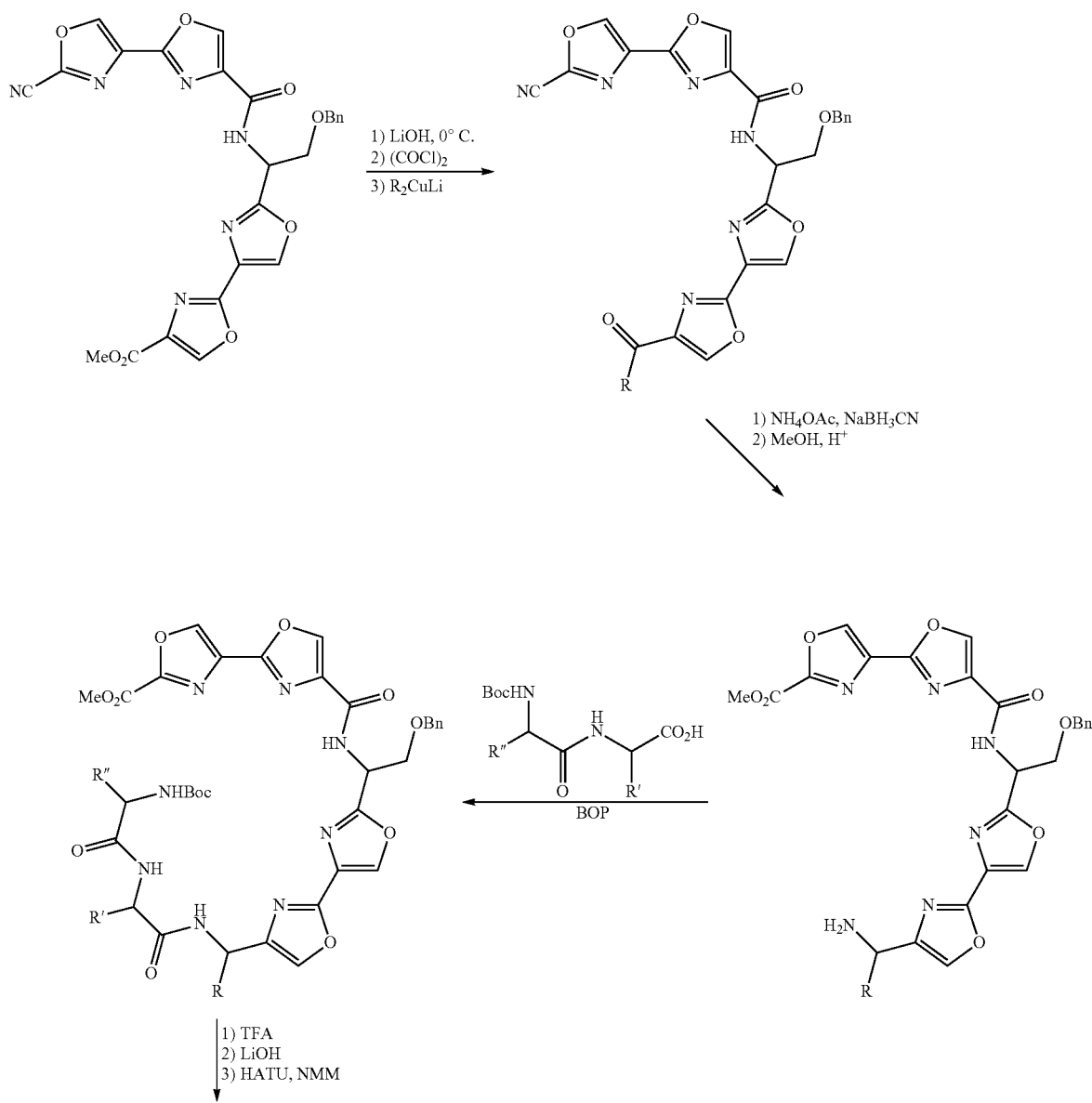

41 42
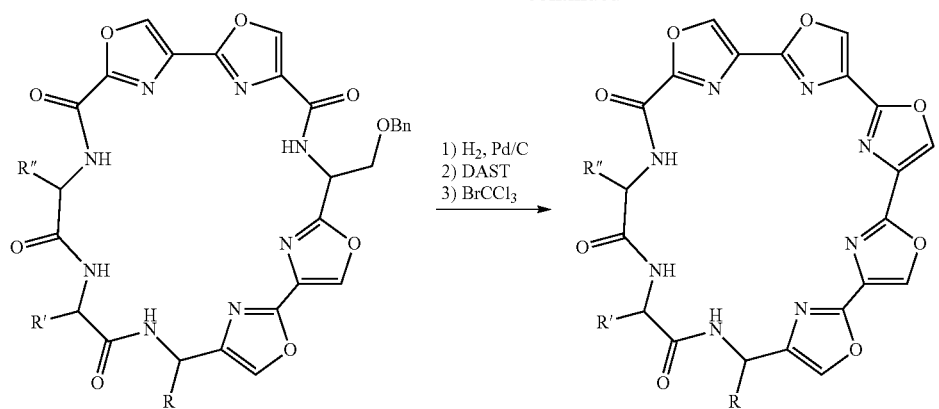
-continued
Scheme 14
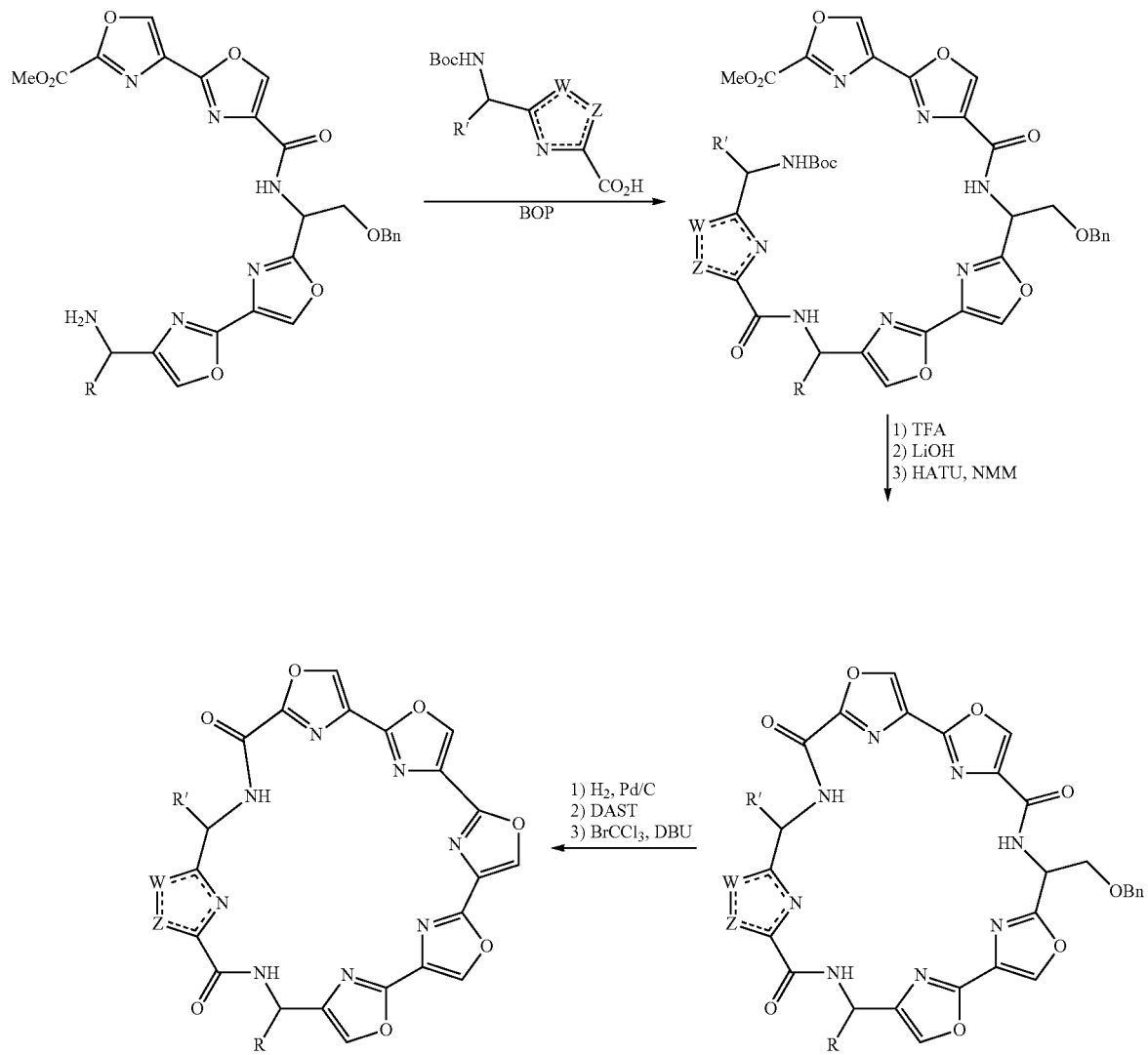

Scheme 15
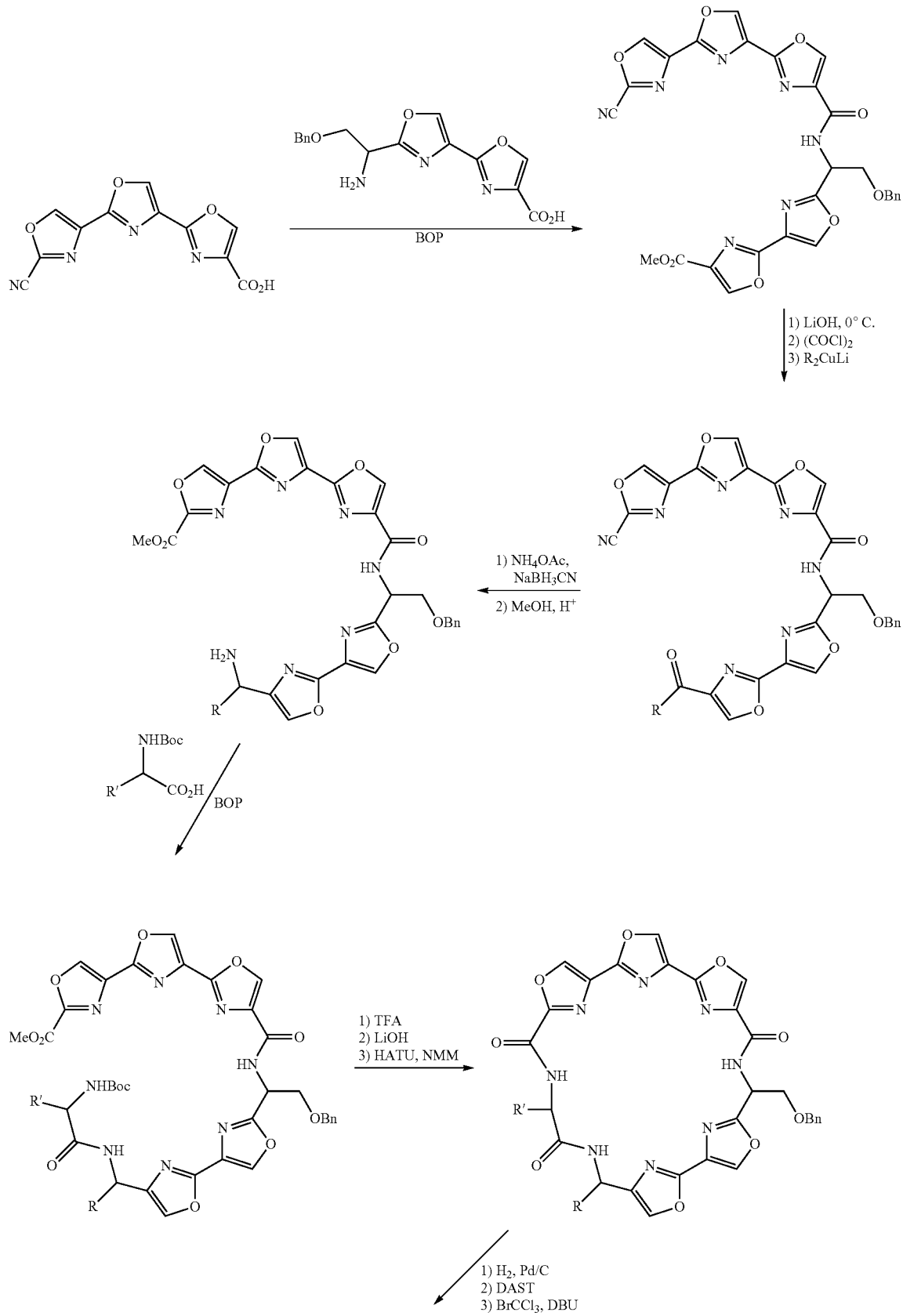

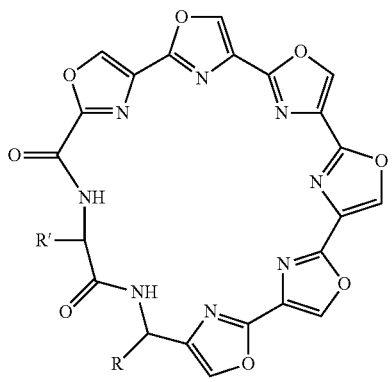

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the invention can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), a vegetable oil, a nontoxic glyceryl ester, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula (I) in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of cancer. Accordingly, in one embodiment the invention also provides a composition comprising a compound of formula (I), or a pharmaceutically acceptable salt thereof, at least one other therapeutic agent, and a pharmaceutically acceptable diluent or carrier. The invention also provides a kit comprising a compound of formula (I), or a pharmaceutically acceptable salt thereof, at least one other therapeutic agent, packaging material, and instructions for administering the compound of the invention or the pharmaceutically acceptable salt thereof and the other therapeutic agent or agents to an animal to treat cancer.

The ability of a compound of the invention to stabilize G-quadroplex DNA may be determined using pharmacological models which are well known to the art, or using Test A described below.

Test A. Stabilization of G-Quadruplex DNA

Analyses can be performed to determine the ability of the agents to bind and thermally stabilize the duplex, triplex, and quadruplex forms of nucleic acids. Toward this end, the UV absorbances of the nucleic acids as a function of temperature in the absence and presence of HXDV is monitored. The melting of duplex and triplex nucleic acids is generally associated with a hyperchromic shift at 260 nm while the melting of quadruplex nucleic acids is associated with a hypochromic shift at 295 nm. Thus, the temperature-dependent absorbances of duplexes and triplexes is monitored at 260 nm, with corresponding quadruplex absorbances being monitored at 295 nm. ST DNA, p(rA).p(rU), p(rA).p(dT), p(dA).2p(dT), p(rA).2p(rU), d($T_2AG_3$)$_4$, and r($UG_4U$) is used as representative models of a DNA duplex, an RNA duplex, a hybrid DNA.RNA duplex, a DNA triplex, an RNA triplex, a DNA quadruplex, and an RNA quadruplex, respectively. All the UV melting studies are conducted at pH 7.5 in the presence of potassium ions.

The ability of compounds to stabilize G-quadroplex DNA may also be determined using Test B described below.

Test B. Temperature-Dependent Spectrophotometry

Temperature-dependent absorption experiments are conducted on an AVIV Model 14DS Spectrophotometer (Aviv Biomedical, Lakewood, N.J.) equipped with a thermoelectrically controlled cell holder. Quartz cells with a pathlength of 1.0 cm are sed for all the absorbance studies. Temperature-dependent absorption profiles are acquired at either 260 (for duplex and triplex) or 295 (for quadruplex) nm with a 5 sec averaging time. The temperature is raised in 0.5° C. increments, and the samples are allowed to equilibrate for 1.5 min at each temperature setting. In the quadruplex melting studies, the concentrations of d($T_2AG_3$)$_4$, 9AP, 15AP, and 21AP are 5 $\mu$M in strand (120 $\mu$M in nucleotide), while the concentration of r($UG_4U$) is 20 $\mu$M in strand (120 $\mu$M in nucleotide).

In the duplex and triplex melting studies, the nucleic acid concentration is 15 μM in base pair (30 μM in nucleotide) or 15 μM in base triple (45 μM in nucleotide) and the HXDV concentration, when present, is 15 μM. The buffer for all the UV melting experiments contains 10 mM EPPS (pH 7.5). In addition, sufficient KCl is added to each solution to bring the total $K^+$ concentration to either 150 mM for $d(T_2AG_3)_4$ and p(rA).p(dT), 2 mM for $r(UG_4U)$, 50 mM for ST DNA, 250 mM for p(dA).2p(dT), or 20 mM for p(rA).2p(rU). Prior to their use in UV melting experiments, all nucleic acid solutions are preheated at 90° C. for 5 min and slowly cooled to room temperature over a period of 4 hr.

The anti-proliferative activity of a compound of the invention may be determined using pharmacological models which are well known to the art, or using Test C described below.

Test C. Evaluation of G-Quadruplex Stabilizers Using the MTT Assay.

Cell lines are selected based upon one or more factors including data on their relative telomerase activity, varied organ sites, available comparative data, and their ability to form solid tumors in athymic nude mice. The advantage of an MTT assay is that the cytotoxic/cytostatic activities can be readily determined. Cells are cultured for 4 days at 37° C. followed by addition of MTT (3-[4,5-dimethylthiozol-2-yl]-2,5-diphenyltetrazolium bromide (Sigma) (0.1 mg/ml). Cells are treated with MTT for 3 hrs and then dissolved in 100 μl 100% DMSO. Absorbance is measured at $OD_{570}$ using a microplate reader (Model 3550 UV from BIO-RAD). The MTT value is normalized to $OD_{570}$ of cells treated with Cellfectin alone. Stock solutions of each compound are prepared. MTT assays are performed using spectrometric analysis and 96 well plates.

The invention will now be illustrated by the following non-limiting Examples.

Example 1

Preparation of Representative Compounds of the Invention

Using procedures similar to those described herein, the following representative compounds of the invention can be prepared.

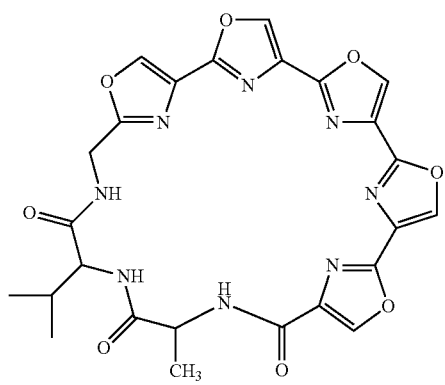

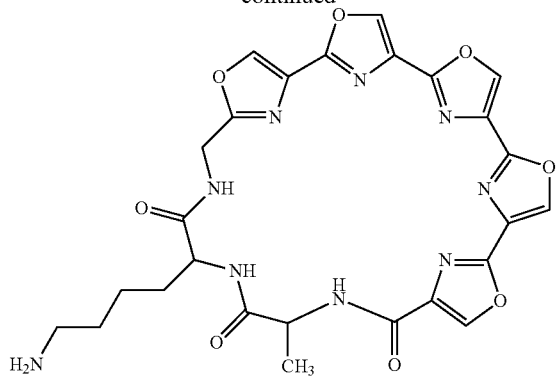

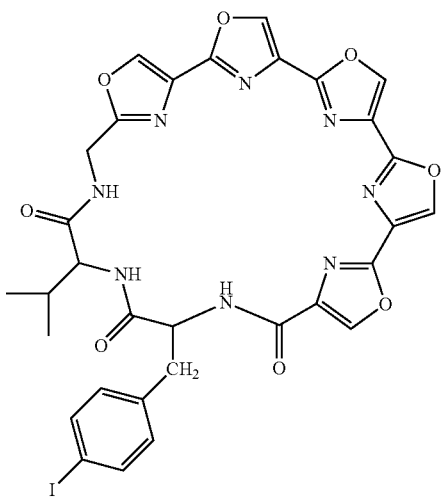

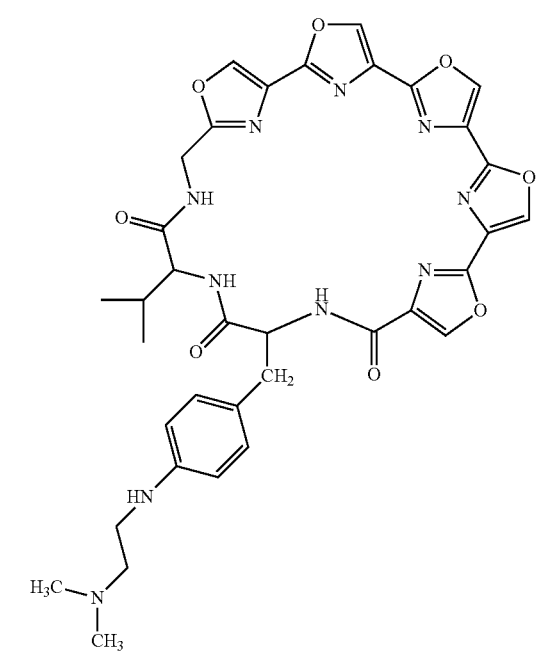

Example 2

Preparation of Representative Compounds of the Invention

Using procedures similar to those described herein, the following representative compounds of the invention can be prepared.

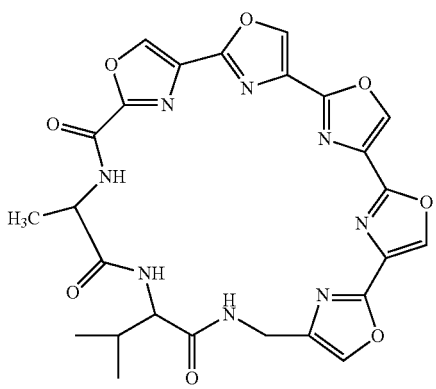

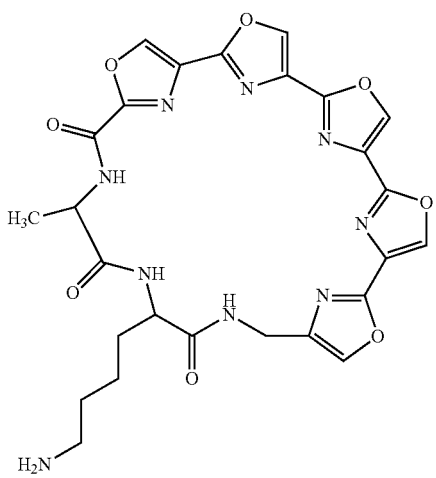

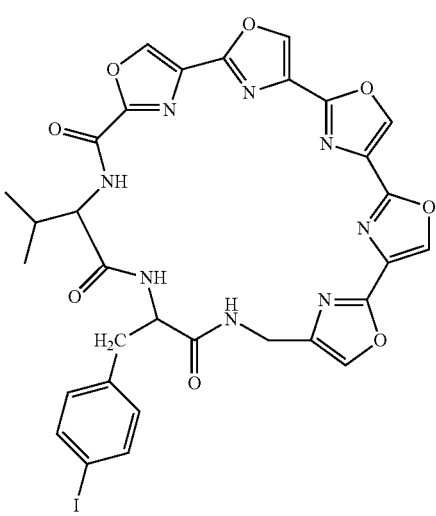

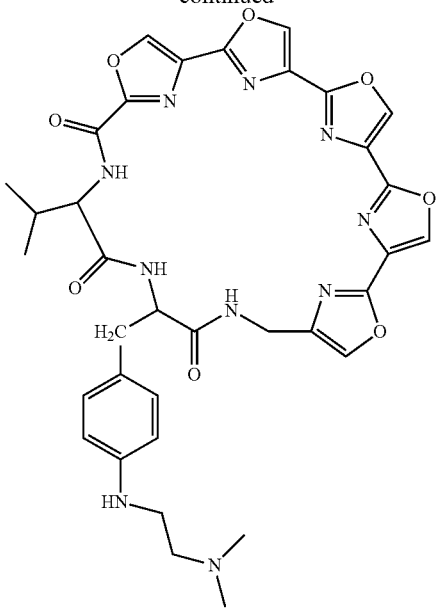

Example 3

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

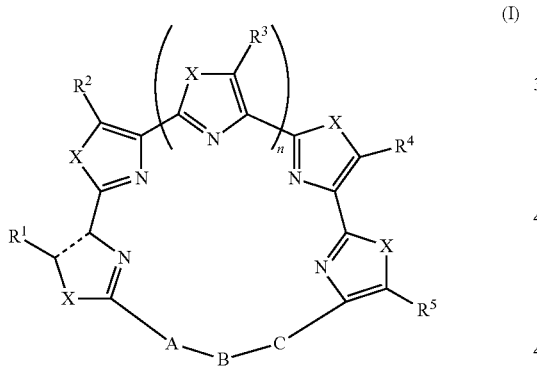

wherein:
the bond represented by ---- is a single or double bond;
A is (—C(=O)NH—CH(R)—)$_x$ or (—CH(R)—NH—C(=O)—)$_x$;
B is a group of formula:

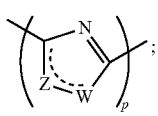

C is (—C(=O)NH—CH(R)—)$_y$ or (—CH(R)—NH—C(=O)—)$_y$;
n is 0, 1 or 2;
p is 0, 1, or 2;
x is 1 or 2;
y is 1 or 2;
provided that the sum of n, p, x and y is 4;
X is O or NH;
one of W and Z is O, S or NH and the other of W and Z is CR$^6$;
each of R$^1$, R$^2$, R$^3$, R$^4$, R$^5$ and R$^6$ is independently hydrogen, (C$_1$-C$_6$)alkyl, (C$_1$-C$_6$)alkoxy, aryl or heteroaryl, wherein each (C$_1$-C$_6$)alkyl and (C$_1$-C$_6$) alkoxy is optionally substituted with OH, (C$_1$-C$_6$) alkoxy, (C$_1$-C$_6$)alkylthio, aryl, NR$^7$R$^8$, or —C(=O) NR$^9$R$^{10}$; and wherein each aryl or heteroaryl is optionally substituted with one or two substituents selected independently from a halo, (C$_1$-C$_6$)alkyl, (C$_1$-C$_6$)alkoxy, NR$^7$R$^8$, and NR$^7$R$^8$(C$_1$-C$_6$)alkyl-;
each R is independently hydrogen, (C$_1$-C$_6$)alkyl, (C$_2$-C$_6$)alkenyl, (C$_1$-C$_6$)alkoxy, aryl or heteroaryl, wherein each (C$_1$-C$_6$)alkyl, (C$_2$-C$_6$)alkenyl and (C$_1$-C$_6$)alkoxy is optionally substituted with OH, (C$_1$-C$_6$) alkoxy, (C$_1$-C$_6$)alkylthio, aryl, NR$^{11}$R$^{12}$, or —C(=O)NR$^{13}$R$^{14}$; and wherein each aryl or heteroaryl is optionally substituted with one or two substituents selected independently from halo, (C$_1$-C$_6$) alkyl, NR$^{11}$R$^{12}$, and NR$^{13}$R$^{14}$(C$_1$-C$_6$)alkyl-;
each of R$^7$ and R$^8$ is independently hydrogen, (C$_1$-C$_6$) alkyl, (C$_1$-C$_6$)alkanoyl, arylcarbonyl, heteroarylcarbonyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$) alkoxycarbony is optionally substituted with one or more NR$^{15}$R$^{16}$; or R$^7$ and R$^8$ together with the nitrogen to which they are attached form a pyrrolidino, piperidino, piperazino, morpholino, thiomorpholino, or azepino ring; and
each of R$^9$ and R$^{10}$ is independently hydrogen, (C$_1$-C$_6$) alkyl, (C$_1$-C$_6$)alkanoyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^9$ and R$^{10}$ together with the nitrogen to which they are attached form a pyrrolidino, piperidino, piperazino, morpholino, thiomorpholino, or azepino ring;
each of R$^{11}$ and R$^{12}$ is independently hydrogen, (C$_1$-C$_6$) alkyl, (C$_1$-C$_6$)alkanoyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^{11}$ and R$^{12}$ together with the nitrogen to which they are attached form a pyrrolidino, piperidino, piperazino, morpholino, thiomorpholino, or azepino ring; and
each of R$^{13}$ and R$^{14}$ is independently hydrogen, (C$_1$-C$_6$) alkyl, (C$_1$-C$_6$)alkanoyl, (C$_1$-C$_6$)alkoxycarbonyl, carbamoyl, N—(C$_1$-C$_6$)alkylaminocarbonyl, aryl or heteroaryl, wherein each (C$_1$-C$_6$)alkyl, (C$_1$-C$_6$)alkanoyl, or (C$_1$-C$_6$)alkoxycarbony is optionally substituted with one or more NR$^{15}$R$^{16}$; or R$^{13}$ and R$^{14}$ together with the nitrogen to which they are attached form a pyrrolidino, piperidino, piperazino, morpholino, thiomorpholino, or azepino ring;
each of R$^{15}$ and R$^{16}$ is independently hydrogen, (C$_1$-C$_6$) alkyl, or (C$_1$-C$_6$)alkanoyl; or R$^{15}$ and R$^{16}$ together with the nitrogen to which they are attached form a pyrrolidino, piperidino, piperazino, morpholino, thiomorpholino, or azepino ring;
or a salt thereof; provided that the compound of formula (I) is not YM-216391.

2. The compound of formula (I) as claimed in claim 1, wherein:

the bond represented by ---- is a single or double bond;

A is $(-C(=O)NH-CH(R)-)_x$ or $(-CH(R)-NH-C(=O)-)_x$;

B is a group of formula:

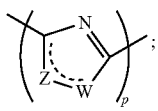

C is $(-C(=O)NH-CH(R)-)_y$ or $(-CH(R)-NH-C(=O)-)_y$;

n is 0, 1 or 2;

p is 0, 1, or 2;

x is 1 or 2;

y is 1 or 2;

provided that the sum of n, p, x and y is 4;

X is O or NH;

one of W and Z is O, S or NH and the other of W and Z is $CR^6$;

each of $R^1$, $R^2$, $R^3$, $R^4$, $R^5$ and $R^6$ is independently hydrogen, $(C_1-C_6)$alkyl, $(C_1-C_6)$alkoxy, aryl or heteroaryl, wherein each $(C_1-C_6)$alkyl and $(C_1-C_6)$alkoxy is optionally substituted with OH, $(C_1-C_6)$alkoxy, $(C_1-C_6)$alkylthio, aryl, $NR^7R^8$, or $-C(=O)NR^9R^{10}$; and wherein each aryl or heteroaryl is optionally substituted with one or two substituents selected independently from a halo, $(C_1-C_6)$alkyl, $NR^7R^8$, and $NR^7R^8(C_1-C_6)$alkyl-;

each R is independently hydrogen, $(C_1-C_6)$alkyl, $(C_1-C_6)$alkoxy, aryl or heteroaryl, wherein each $(C_1-C_6)$alkyl and $(C_1-C_6)$alkoxy is optionally substituted with OH, $(C_1-C_6)$alkoxy, $(C_1-C_6)$alkylthio, aryl, $NR^{11}R^{12}$, or $-C(=O)NR^{13}R^{14}$; and wherein each aryl or heteroaryl is optionally substituted with one or two substituents selected independently from halo, $(C_1-C_6)$alkyl, $NR^{11}R^{12}$, and $NR^{13}R^{14}(C_1-C_6)$alkyl-;

each of $R^7$ and $R^8$ is independently hydrogen, $(C_1-C_6)$alkyl, $(C_1-C_6)$alkanoyl, $(C_1-C_6)$alkoxycarbonyl, carbamoyl, N—$(C_1-C_6)$alkylaminocarbonyl aryl or heteroaryl, wherein each $(C_1-C_6)$alkyl, $(C_1-C_6)$alkanoyl, or $(C_1-C_6)$alkoxycarbony is optionally substituted with one or more $NR^{15}R^{16}$; or $R^7$ and $R^8$ together with the nitrogen to which they are attached form a pyrrolidino, piperidino, piperazino, morpholino, thiomorpholino, or azepino ring; and each of $R^9$ and $R^{10}$ is independently hydrogen, $(C_1-C_6)$alkyl, $(C_1-C_6)$alkanoyl, $(C_1-C_6)$alkoxycarbonyl, carbamoyl, N—$(C_1-C_6)$alkylaminocarbonyl, aryl or heteroaryl, wherein each $(C_1-C_6)$alkyl, $(C_1-C_6)$alkanoyl, or $(C_1-C_6)$alkoxycarbony is optionally substituted with one or more $NR^{15}R^{16}$; or $R^9$ and $R^{10}$ together with the nitrogen to which they are attached form a pyrrolidino, piperidino, piperazino, morpholino, thiomorpholino, or azepino ring;

each of $R^{11}$ and $R^{12}$ is independently hydrogen, $(C_1-C_6)$alkyl, $(C_1-C_6)$alkanoyl, $(C_1-C_6)$alkoxycarbonyl, carbamoyl, N—$(C_1-C_6)$alkylaminocarbonyl, aryl or heteroaryl, wherein each $(C_1-C_6)$alkyl, $(C_1-C_6)$alkanoyl, or $(C_1-C_6)$alkoxycarbony is optionally substituted with one or more $NR^{15}R^{16}$; or $R^{11}$ and $R^{12}$ together with the nitrogen to which they are attached form a pyrrolidino, piperidino, piperazino, morpholino, thiomorpholino, or azepino ring; and each of $R^{13}$ and $R^{14}$ is independently hydrogen, $(C_1-C_6)$alkyl, $(C_1-C_6)$alkanoyl, $(C_1-C_6)$alkoxycarbonyl, carbamoyl, N—$(C_1-C_6)$alkylaminocarbonyl, aryl or heteroaryl, wherein each $(C_1-C_6)$alkyl, $(C_1-C_6)$alkanoyl, or $(C_1-C_6)$alkoxycarbony is optionally substituted with one or more $NR^{15}R^{16}$; or $R^{13}$ and $R^{14}$ together with the nitrogen to which they are attached form a pyrrolidino, piperidino, piperazino, morpholino, thiomorpholino, or azepino ring;

each of $R^{15}$ and $R^{16}$ is independently hydrogen, $(C_1-C_6)$alkyl, or $(C_1-C_6)$alkanoyl; or $R^{15}$ and $R^{16}$ together with the nitrogen to which they are attached form a pyrrolidino, piperidino, piperazino, morpholino, thiomorpholino, or azepino ring;

or a salt thereof; provided that the compound of formula (I) is not YM-216391.

3. The compound as claimed in claim 1, in which the bond represented by ---- is a double bond.

4. The compound as claimed in claim 1, which is of the formula (I')

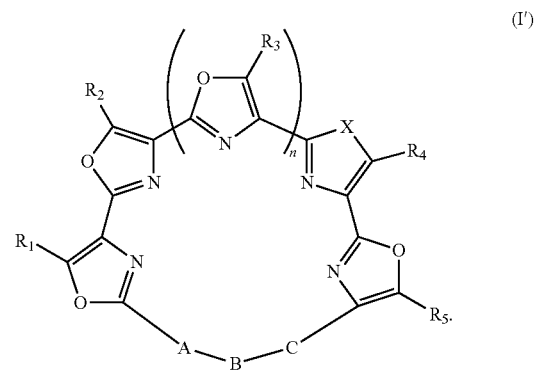

5. The compound as claimed in claim 1, in which each X is O.

6. The compound as claimed in claim 1, in which each R is selected independently from hydrogen, methyl, isopropyl, 1-methylpropyl, 2-methylpropyl and benzyl.

7. A compound as claimed in claim 1 in which each R is selected independently from $(C_1-C_6)$alkyl or $(C_2-C_6)$alkenyl wherein each $(C_1-C_6)$alkyl and $(C_2-C_6)$alkenyl, is optionally substituted with $NR^{11}R^{12}$.

8. A compound as claimed in claim 1 in which each R is selected independently from aminomethyl, 2-aminoethyl, 3-aminopropyl or 4-aminobutyl.

9. The compound as claimed in claim 1, in which A is $-C(=O)NH-CH(R)-$.

10. The compound as claimed in claim 1, in which A is $-C(=O)NH-CH(R)-C(=O)NH-CH(R)-$.

11. The compound as claimed in claim 1, in which A is $-C(=O)NH-CH_2-$.

12. The compound as claimed in claim 1, in which A is $-C(=O)NH-CH_2-C(=O)NH-CH_2-$.

13. The compound as claimed in claim 1, in which A is $-CH(R)-NH-C(=O)-$.

14. The compound as claimed in claim 1, in which A is $-CH(R)-NH-C(=O)-CH(R)-NH-C(=O)-$.

15. The compound as claimed in claim 1, in which A is $-CH_2-NH-C(=O)-$.

16. The compound as claimed in claim 1, in which A is $-CH_2NH-C(=O)-CH_2-NH-C(=O)-$.

17. The compound as claimed in claim 1, which is of the formula:
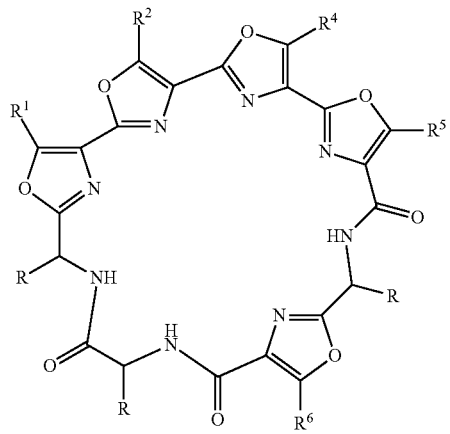
(Ia)
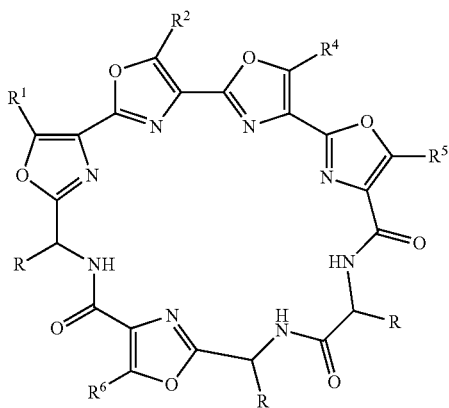
(Ib)
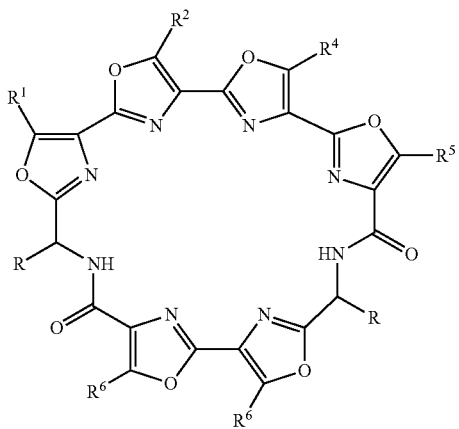
(Ic)
-continued
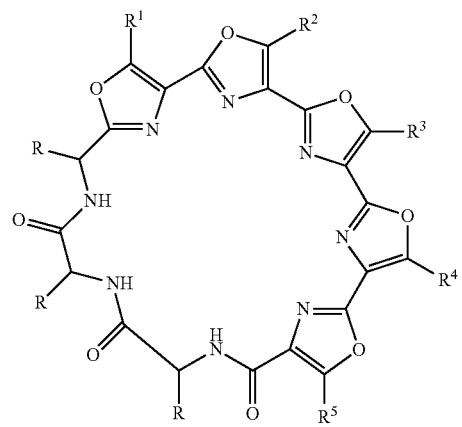
(Id)
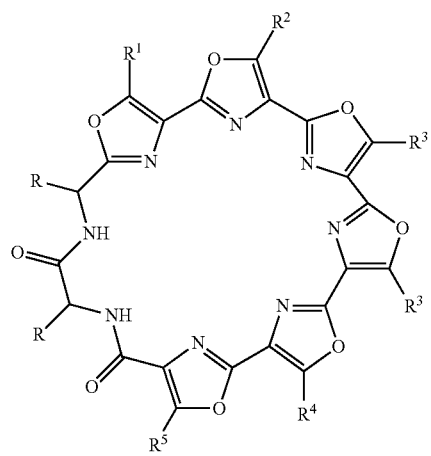
(Ie)
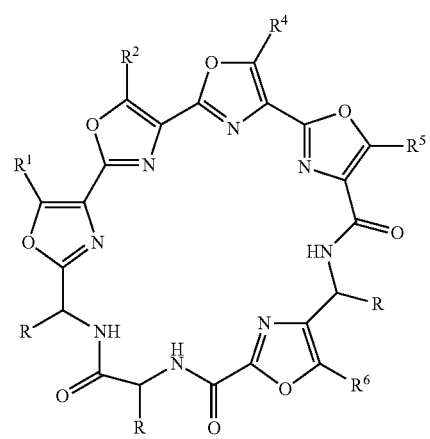
(If)

(Ig)
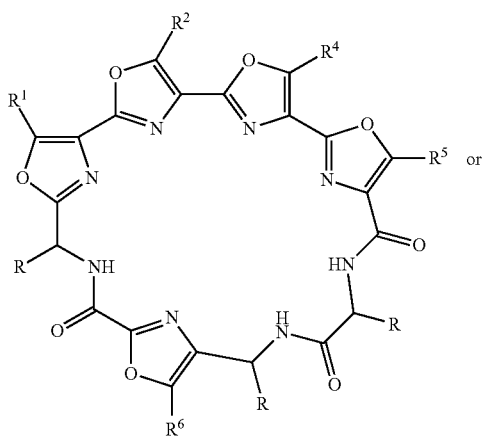
(Ih)
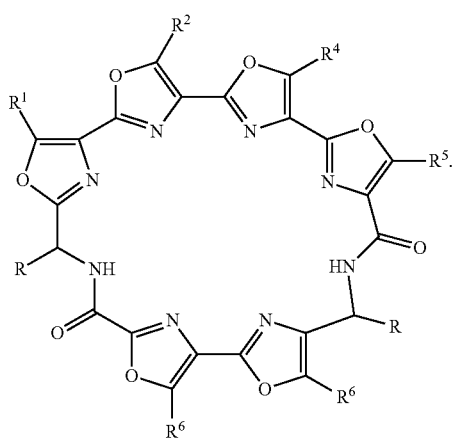
18. The compound as claimed in claim 1, which is of the formula:
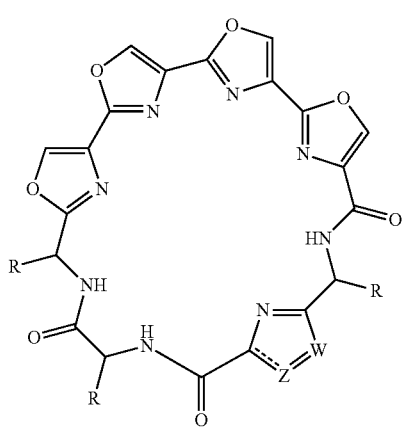
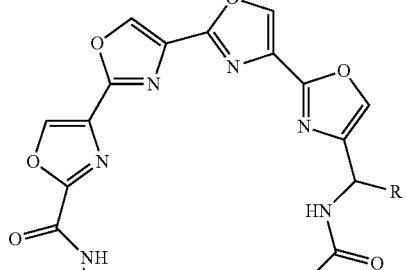
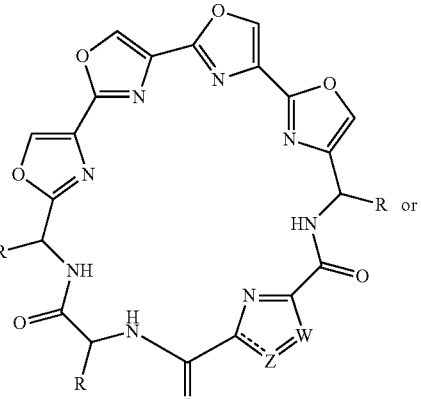 or
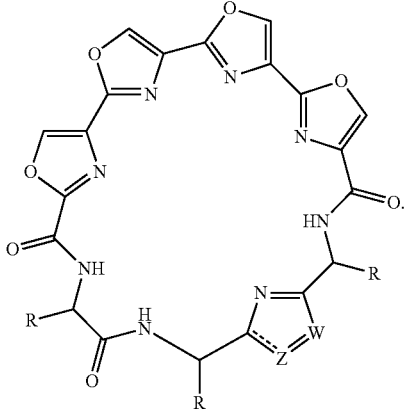
19. The compound as claimed in claim 1, which is of the formula:
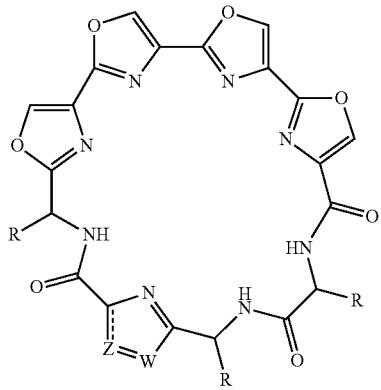

-continued
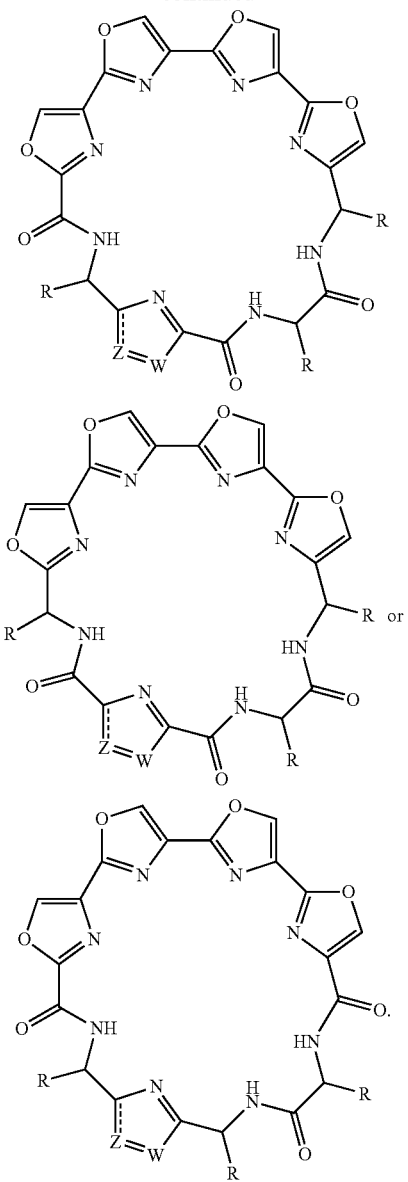
20. The compound as claimed in claim 1, which is of the formula:
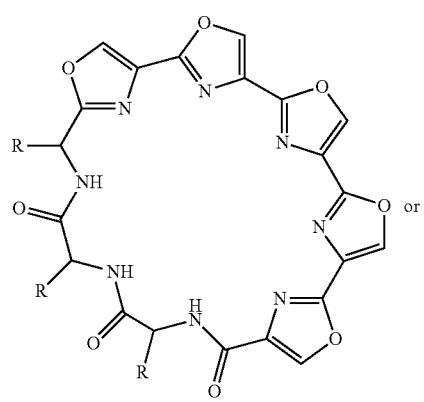
-continued
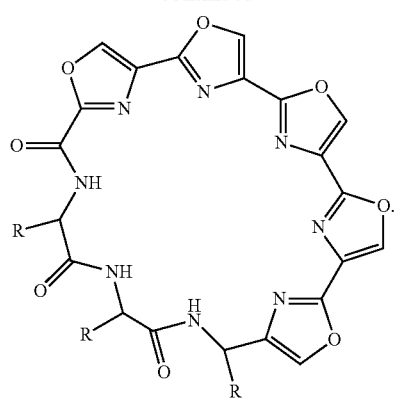
21. The compound as claimed in claim 1, which is of the formula:
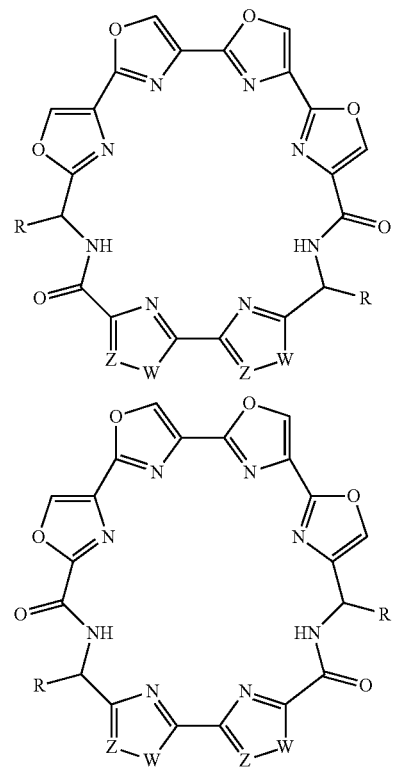
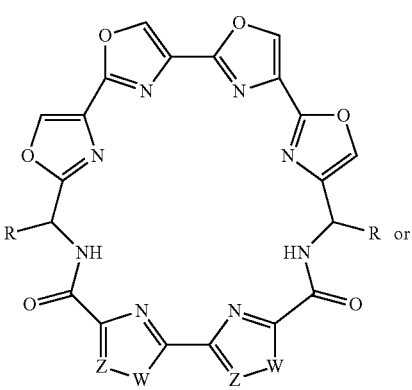

-continued
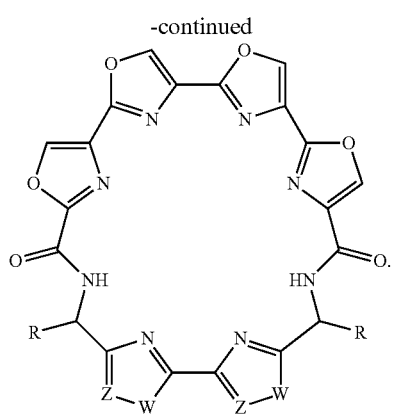
22. The compound as claimed in claim 1, which is of the formula:
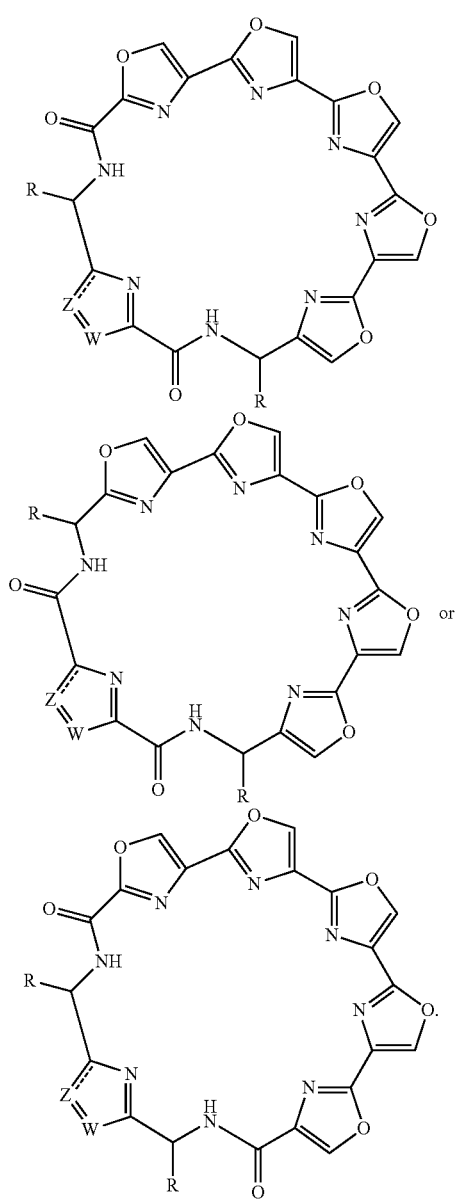
23. The compound as claimed in claim 1, which is of the formula:
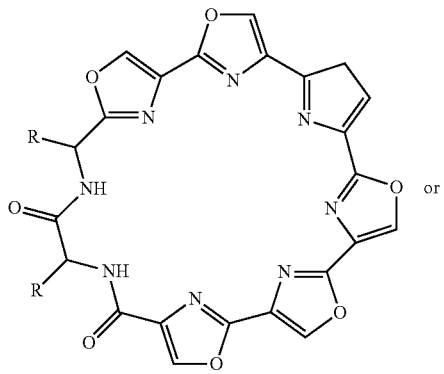
or
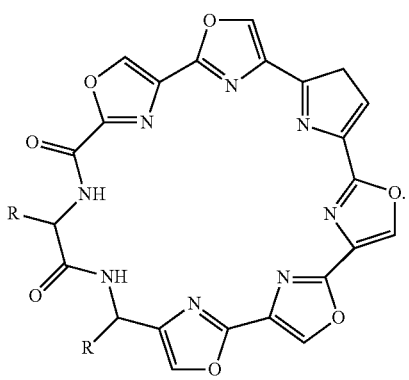
24. The compound of claim 18 wherein W is O or S and Z is $CR^6$.
25. The compound of claim 18 wherein Z is O or S and W is $CR^6$.
26. The compound of claim 1 wherein the compound of formula (I) is not a compound of the following formula:
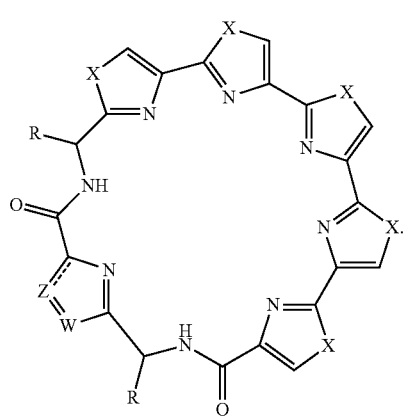

27. The compound of claim 1 wherein the compound of formula (I) is not a compound of the following formula:

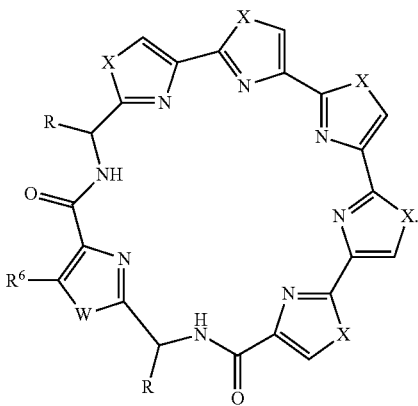

28. A compound of formula (II) or (III):

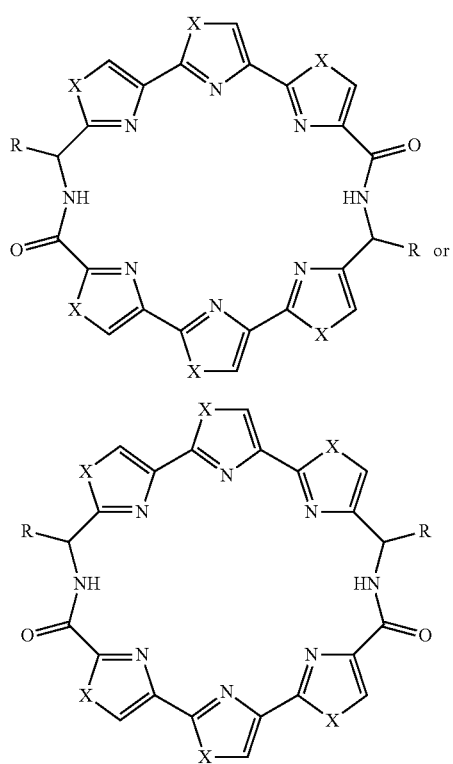

wherein:
each X is independently O, S or NH;
each R is independently hydrogen, $(C_1-C_6)$alkyl, $(C_2-C_6)$alkenyl, $(C_1-C_6)$alkoxy, aryl or heteroaryl, wherein each $(C_1-C_6)$alkyl, $(C_2-C_6)$alkenyl and $(C_1-C_6)$alkoxy is optionally substituted with OH, $(C_1-C_6)$alkoxy, $(C_1-C_6)$alkylthio, aryl, $NR^{11}R^{12}$, or $—C(=O)NR^{13}R^{14}$; and wherein each aryl or heteroaryl is optionally substituted with one or two substituents selected independently from halo, $(C_1-C_6)$alkyl, $NR^{11}R^{12}$ and $NR^{13}R^{14}(C_1-C_6)$alkyl-;
each of $R^{11}$ and $R^{12}$ is independently hydrogen, $(C_1-C_6)$alkyl, $(C_1-C_6)$alkanoyl, $(C_1-C_6)$alkoxycarbonyl, carbamoyl, N—$(C_1-C_6)$alkylaminocarbonyl, aryl or heteroaryl, wherein each $(C_1-C_6)$alkyl, $(C_1-C_6)$alkanoyl, or $(C_1-C_6)$alkoxycarbony is optionally substituted with one or more $NR^{15}R^{16}$; or $R^{11}$ and $R^{12}$ together with the nitrogen to which they are attached form a pyrrolidino, piperidino, piperazino, morpholino, thiomorpholino, or azepino ring; and each of $R^{13}$ and $R^{14}$ is independently hydrogen, $(C_1-C_6)$alkyl, $(C_1-C_6)$alkanoyl, $(C_1-C_6)$alkoxycarbonyl, carbamoyl, N—$(C_1-C_6)$alkylaminocarbonyl, aryl or heteroaryl, wherein each $(C_1-C_6)$alkyl, $(C_1-C_6)$alkanoyl, or $(C_1-C_6)$alkoxycarbony is optionally substituted with one or more $NR^{15}R^{16}$; or $R^{13}$ and $R^{14}$ together with the nitrogen to which they are attached form a pyrrolidino, piperidino, piperazino, morpholino, thiomorpholino, or azepino ring;

each of $R^{15}$ and $R^{16}$ is independently hydrogen, $(C_1-C_6)$alkyl or $(C_1-C_6)$alkanoyl; or $R^{15}$ and $R^{16}$ together with the nitrogen to which they are attached form a pyrrolidino, piperidino, piperazino, morpholino, thiomorpholino, or azepino ring;

or a salt thereof.

29. The compound of claim 28 wherein each R is independently hydrogen, $(C_1-C_6)$alkyl, $(C_1-C_6)$alkoxy, aryl or heteroaryl, wherein each $(C_1-C_6)$alkyl and $(C_1-C_6)$alkoxy is optionally substituted with OH, $(C_1-C_6)$alkoxy, $(C_1-C_6)$alkylthio, aryl, $NR^{11}R^{12}$, or $—C(=O)NR^{13}R^{14}$; and wherein each aryl or heteroaryl is optionally substituted with one or two substituents selected independently from halo, $(C_1-C_6)$alkyl, $NR^{11}R^{12}$, and $NR^{13}R^{14}(C_1-C_6)$alkyl-.

30. The compound of claim 28 wherein each X is O.

31. The compound of claim 28 wherein each R is H.

32. The compound of claim 1 which is,

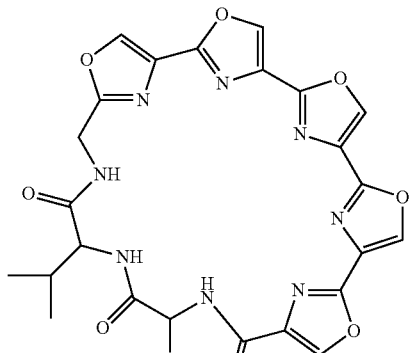

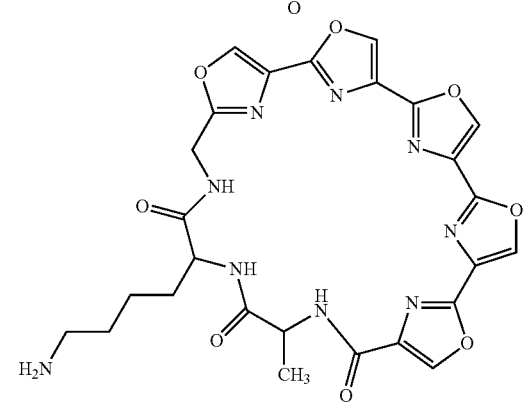

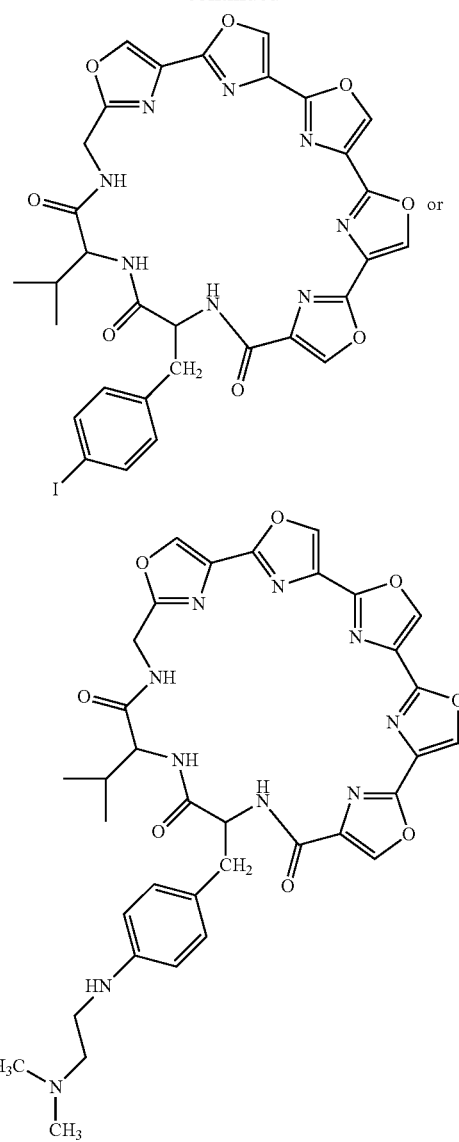
or a salt thereof.
33. The compound of claim 1 which is,
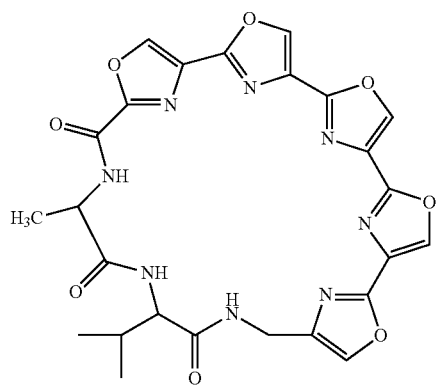
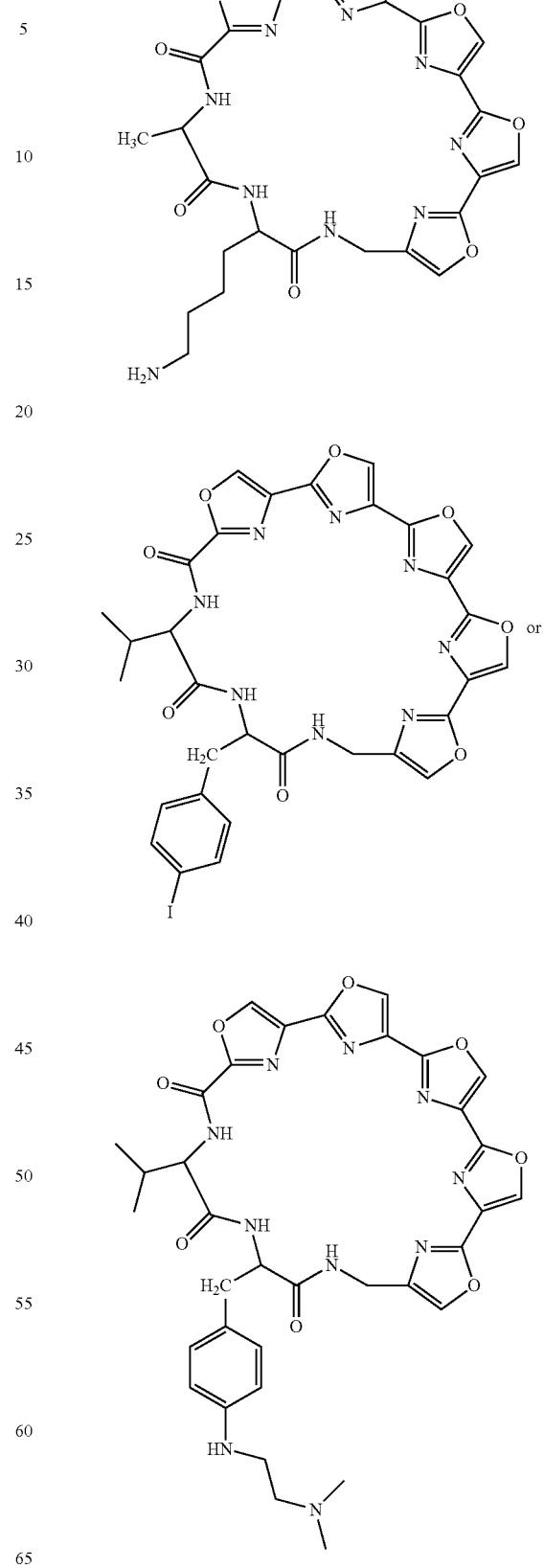
or a salt thereof.

34. A pharmaceutical composition comprising a compound of formula (I) as defined in claim 1; or a pharmaceutically acceptable salt thereof; and a pharmaceutically acceptable carrier.

35. A method to stabilize G-quadruplex DNA comprising contacting the G-quadruplex DNA with a compound of formula (I) as defined in claim 1, or a salt thereof.

* * * * *